(12) United States Patent
Endo et al.

(10) Patent No.: US 8,428,737 B2
(45) Date of Patent: Apr. 23, 2013

(54) MOVEMENT ASSIST SYSTEM

(75) Inventors: Yosuke Endo, Wako (JP); Ken Yasuhara, Wako (JP); Kei Shimada, Wako (JP); Eiichi Genda, Nagoya (JP)

(73) Assignee: Honda Motor Co., Ltd., Tokyo (JP)

( * ) Notice: Subject to any disclaimer, the term of this patent is extended or adjusted under 35 U.S.C. 154(b) by 999 days.

(21) Appl. No.: 12/198,503

(22) Filed: Aug. 26, 2008

(65) Prior Publication Data

US 2009/0062884 A1   Mar. 5, 2009

Related U.S. Application Data

(60) Provisional application No. 60/968,223, filed on Aug. 27, 2007.

(30) Foreign Application Priority Data

Oct. 15, 2007 (JP) .................................. 2007-268338

(51) Int. Cl.
*A61N 1/00* (2006.01)
(52) U.S. Cl.
USPC .......................................................... 607/49
(58) Field of Classification Search .................... 607/48, 607/49
See application file for complete search history.

(56) References Cited

U.S. PATENT DOCUMENTS 4,499,900 A * 2/1985 Petrofsky et al. ................ 607/48
5,476,441 A * 12/1995 Durfee et al. .................... 602/23

FOREIGN PATENT DOCUMENTS

JP 2005-073935 3/2005
JP 2007-061217 3/2007

* cited by examiner

*Primary Examiner* — Niketa Patel
*Assistant Examiner* — Alyssa M Alter
(74) *Attorney, Agent, or Firm* — Rankin, Hill & Clark LLP

(57) ABSTRACT

A movement assist system for assisting stably a movement of a creature, particularly a creature whose body part is paralyzed due to neuropathy or the like. According to the movement assist system, walking movement of a human is assisted according to an output from an actuator of a movement assist device. A timing of an electrical stimulation applied to the creature is adjusted by an electrical stimulation device on the basis of a signal representing an arithmetic processing result by a first controller which controls the output of the actuator. According thereto, it is possible to apply an electrical stimulation to the human at an appropriate timing from the viewpoint of maintaining an appropriate posture by considering a periodical movement state of the human even in cases where the body function is degraded, allowing the human assisted by the movement assist device to continue the walking movement.

7 Claims, 13 Drawing Sheets

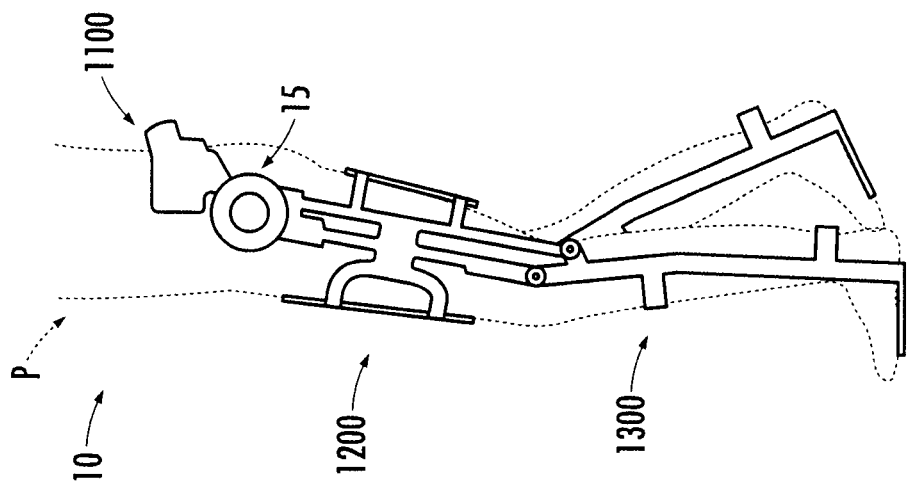
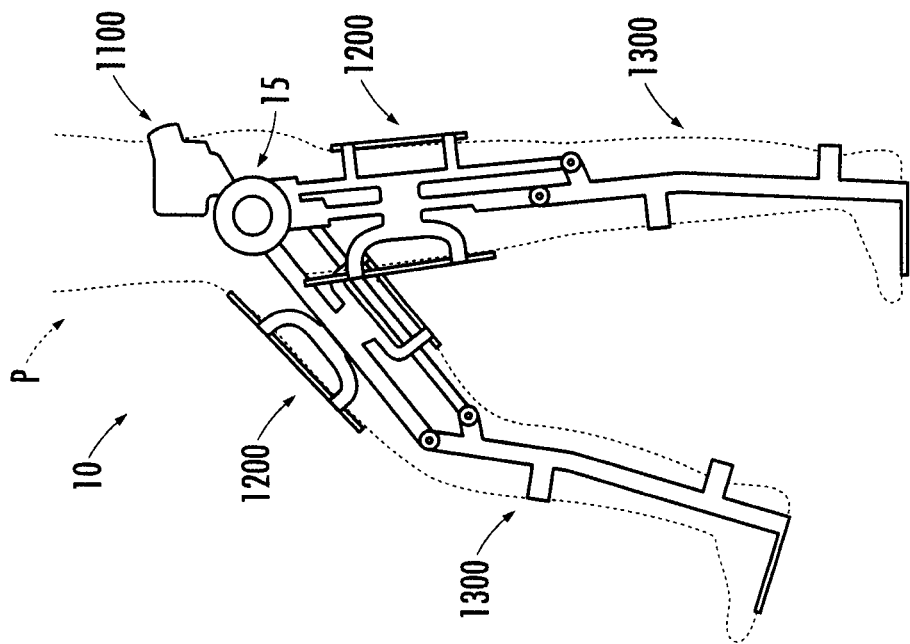
FIG.5 (a)
FIG.5 (b)

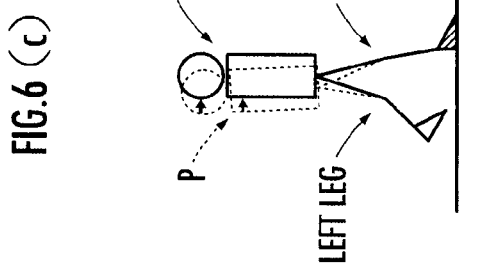
FIG.6 (a)
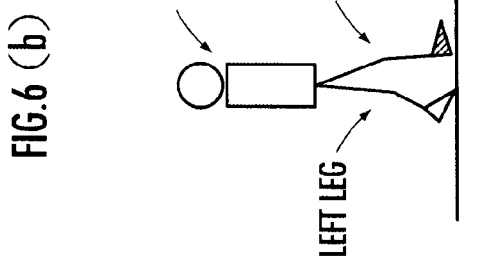
FIG.6 (b)
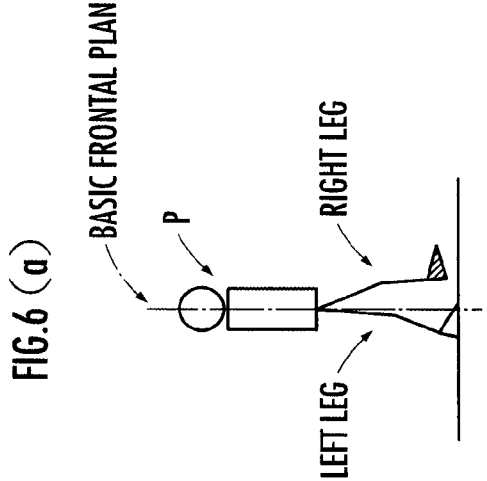
FIG.6 (c)
FIG.6 (d)
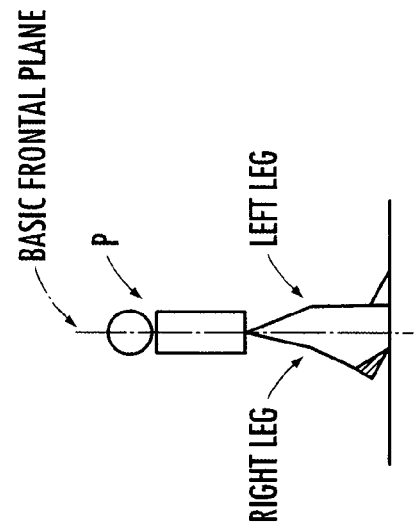
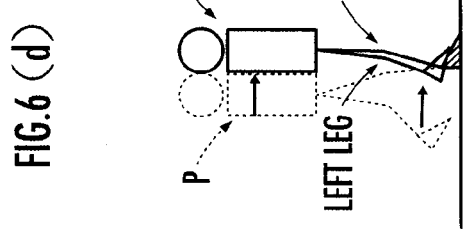
FIG.6 (e)

c

ε

MOVEMENT ASSIST SYSTEM

BACKGROUND OF THE INVENTION

1. Field of the Invention

The present invention relates to a movement assist system for assisting a creature in moving.

2. Description of the Related Art

There has been disclosed a technique to recover motor ability of a patient whose body part such as the lower limb or the like is paralyzed due to neuropathy by applying an electrical stimulation to the patient via a functional electrical stimulation device (FES device). Further, there has been disclosed in Japanese Patent Laid-open No. 2005-073935 a technique which controls the timing of the electrical stimulation by the FES device or an electrical stimulation device on the basis of a posture or an action of the patient to assure a safety walking for the patient. Furthermore, there has been disclosed in Japanese Patent Laid-open No. 2007-061217 a device which assists or guides a human in walking movement involving a movement of a thigh by applying a force respectively to the waist and the thigh via an orthosis, namely an outfit.

However, there is a variation on response of a human body with respect to an electrical stimulation, which brings about a difficulty in assisting stably a human in moving. Moreover, even though a force is applied to a human body, it still results in a difficulty in assisting stably a human in moving if the natural strength in the human that should be brought out is not sufficiently exploited.

SUMMARY OF THE INVENTION

The present invention has been accomplished in view of the aforementioned problems, and it is therefore an objective of the present invention to provide a movement assist system for assisting stably a movement of a creature (for example, an animal or a human), particularly a creature whose body part is paralyzed due to neuropathy or the like.

The movement assist system according to a first invention includes a movement assist device; and an electrical stimulation device; wherein the movement assist device includes an orthosis (outfit) mounted on the creature, an actuator connected to the orthosis, and a first controller which controls an amplitude and a phase of an output from the actuator, and assists the creature in a periodical movement by applying an output which varies periodically from the actuator to the creature via the orthosis; and the electrical stimulation device includes an electrode attached to the creature and a second controller which adjusts an electrical stimulation applied to the creature on the basis of an output signal from the first controller or an output signal representing a movement state of the creature from a sensor, and assists the creature in producing a physical strength by applying the electrical stimulation to the creature via the electrode.

According to the movement assist system of the first invention, the movement assist device assists the creature in a periodical movement by applying an output from the actuator which varies periodically to the creature via the orthosis. The electrical stimulation applied to the creature is adjusted on the basis of the output signal representing the arithmetic processing result (operation processing result) of the first controller or the output signal from the sensor. The arithmetic processing result of the first controller is the primary determination factor of the output from the control object thereof, namely the actuator, and the periodical movement state of the creature assisted by the output. Therefore, it is possible to apply an electrical stimulation to the creature at an appropriate timing (or timing and magnitude) from the viewpoint of maintaining an appropriate posture by considering the periodical movement state of the creature even in cases where the body function is degraded due to neuropathy or the like, allowing the creature assisted by the movement assist device to continue the periodical movement with the posture stably maintained. Thereby, the periodical movement of the creature whose body part is paralyzed or whose body function is degraded due to such as neuropathy may be stably assisted.

The movement assist system according to a second invention is depended on the movement assist system of the first invention, wherein the first controller includes a movement vibrator determination element for determining a second movement vibrator which varies periodically according to a physical movement of the creature, and a second vibrator generation element for generating a second vibrator, which serves as a control basis on the output of the actuator, as an output vibration signal from a second model by inputting the second movement vibrator determined by the movement vibrator determination element as an input vibration signal to the second model which generates the output vibration signal varying at a specific angular velocity defined according to a second intrinsic angular velocity on the basis of the input vibration signal; and the second controller adjusts the electrical stimulation applied to the creature on the basis of the output signal from the first controller which represents an arithmetic processing result of the second vibrator generation element.

According to the movement assist system of the second invention, the electrical stimulation applied to the creature may be adjusted on the basis of the output signal representing the arithmetic processing result of the second vibrator generation element. The arithmetic processing result of the second vibrator generation element for generating the second vibrator which is the control basis of the output from the actuator is the primary determination factor of the periodical movement state of the creature. Therefore, it is possible to apply an electrical stimulation to the creature at an appropriate timing and magnitude from the viewpoint of maintaining an appropriate posture by considering the periodical movement state of the creature even in cases where the body function is degraded due to neuropathy or the like, allowing the creature assisted by the movement assist device to continue the periodical movement with the posture stably maintained.

The movement assist system according to a third invention is depended on the movement assist system of the second invention, wherein the movement vibrator determination element determines a first movement vibrator which varies periodically according to the physical movement of the creature; the first controller includes a first vibrator generation element for generating a first vibrator as an output vibration signal from a first model by inputting the first movement vibrator determined by the movement vibrator determination element as an input vibration signal to the first model which generates the output vibration signal varying at a specific angular velocity defined according to a first intrinsic angular velocity on the basis of the input vibration signal by entraining to the input vibration signal (synchronization phenomenon); and an intrinsic angular velocity setting element for setting an angular velocity of a second virtual vibrator as the second intrinsic velocity according to a virtual model representing a first virtual vibrator and a second virtual vibrator which interact and vary periodically with a second phase difference on the basis of a first phase difference between the first movement vibrator determined by the movement vibrator determination element and the first vibrator generated by the first vibrator generation element so as to approximate the second phase difference to a desired phase difference.

According to the movement assist system of the third invention, the first vibrator varying periodically is generated at a rhythm which is conditioned to a rhythm of the periodical movement of the creature, and the second intrinsic angular velocity is set on the basis of the first phase difference representing a deviation between the two rhythms. Thereby, by considering the periodical movement state (specified by the magnitude and phase) of the creature, the magnitude and the phase of the force applied to the creature by the movement assist device may be appropriately controlled. Moreover, as aforementioned, the electrical stimulation applied to the creature is adjusted on the basis of the output signal representing the arithmetic processing result of the second vibrator generation element. According thereto, it is possible to apply an electrical stimulation to the creature at an appropriate timing and magnitude from the viewpoint of maintaining an appropriate posture by considering the periodical movement state of the creature even in cases where the body function is degraded due to neuropathy or the like, allowing the creature assisted by the movement assist device to continue the periodical movement with the posture stably maintained.

The movement assist system according to a fourth invention is depended on the movement assist system of the second invention, wherein the first controller includes a movement variable determination element for obtaining a determination value of a movement variable which represents a scale magnitude of the periodical movement of the creature; and the second vibrator generation element corrects the second model so as to approximate the determination value of the movement variable determined by the movement variable determination element to a desired value.

According to the movement assist system of the fourth invention, the second model is corrected so as to approximate the value of the movement variable which is a function of the magnitude (movement scale) of the periodical movement of the creature. Thereafter, the second vibrator is generated according to the corrected second model, and the periodical force applied to the creature is controlled on the basis of the second vibrator. According thereto, in spite of the rhythm speed of the periodical movement of the creature, the periodical movement can be assisted by applying a force with an appropriate magnitude to the creature so as to make the movement scale match the desired movement scale.

The movement assist system according to a fifth invention is depended on the movement assist system of the fourth invention, wherein the second model is defined by a simultaneous differential equation having multiple state variables representing a behavior state of the creature, which contains a product of the desired value of the movement variable and a coefficient; and the second vibrator generation element generates the second vibrator on the basis of values of the state variables obtained by solving the simultaneous differential equation, and corrects the second model by correcting the coefficient so as to approximate the determination value of the movement variable obtained by the movement variable determination element to the desired value.

According to the movement assist system of the fifth invention, the product of the desired value of the movement variable which is a function of the magnitude of the periodical movement of the creature and the coefficient is contained in the simultaneous differential equation which represents the behavior state of the body part of the creature and defines the second model, and the second model is corrected by correcting the coefficient. Thereafter, the second vibrator is generated on the basis of the values of the multiple state variables which are the solutions of the simultaneous differential equation which defines the corrected second model, and a periodical force applied to the creature is controlled on the basis of the second vibrator. According thereto, in spite of the rhythm speed of the periodical movement of the creature, the periodical movement can be assisted by applying a force with an appropriate magnitude to the creature so as to make the movement scale match the desired movement scale.

The movement assist system according to a sixth invention is depended on the movement assist system of the second invention further includes an adjusting device, wherein the second model is defined by a simultaneous differential equation which contains multiple state variables representing a behavior state of the creature, and the value of a member or a coefficient in the simultaneous differential equation is adjusted by the adjusting device.

According to the movement assist system of the sixth invention, since no other model but the second model is used, therefore the arithmetic processing load needed to generate the second vibrator may be alleviated accordingly. Moreover, the value of a member or a coefficient contained in the simultaneous differential equation of the state variables for defining the second model is adjusted by the adjusting device and the second model is used to generate the second vibrator. Thereafter, the second vibrator is generated according to the adjusted second model, and a periodical force applied to the creature is controlled on the basis of the second vibrator. According thereto, the periodical movement of the creature can be assisted by applying a force to the creature so as to make the movement scale and the movement rhythm thereof match the desired movement scale and the desired movement rhythm, respectively, with an attempt to alleviate the arithmetic processing load meanwhile.

The movement assist system according to a seventh invention is depended on the movement assist system of the sixth invention, wherein the simultaneous differential equation for defining the second model includes a time constant representing a variation pattern of the state variables; and the time constant value is adjusted by the adjusting device.

According to the movement assist system of the seventh invention, the time constant is adjusted via the adjusting device and the time constant represents the variation pattern of the state variables representing the behavior state of the creature. According thereto, the periodical variation pattern of each of the second vibrator and output from the actuator may be adjusted, thus, it is possible to assist the periodical movement so as to approximate the locomotor rhythm of the creature assisted according to the output from the actuator 15 to the desired locomotor rhythm.

The movement assist system according to an eighth invention is depended on the movement assist system of the sixth invention, wherein the simultaneous differential equation for defining the second model includes a coefficient relative to the desired value of the movement variable representing the movement scale of the creature; and the value of the coefficient is adjusted by the adjusting device.

According to the movement assist system of the eighth invention, the coefficient relative to the desired value of the movement variable representing the movement scale of the creature is adjusted via the adjusting device. The coefficient is contained in the simultaneous differential equation for defining the second model. According thereto, a magnitude of a basic vibrator and the magnitude of the output from the actuator may be adjusted; thereby, the periodical movement thereof may be assisted so as to approximate the movement scale of the creature to the desired movement scale.

The movement assist system according to a ninth invention is depended on the movement assist system of the first invention, wherein the second controller adjusts the electrical stimulation applied to the creature on the basis of a signal representing a posture of the creature which serves as the movement state of the creature.

According to the movement assist system of the ninth invention, it is possible to apply an electrical stimulation to the creature at an appropriate timing and magnitude from the viewpoint of maintaining an appropriate posture by considering the periodical movement state of the creature even in cases where the body function is degraded due to neuropathy or the like, allowing the creature assisted by the movement assist device to continue the periodical movement with the posture stably maintained.

The movement assist system according to a tenth invention is depended on the movement assist system of the first invention and further includes a load alleviation equipment which supports a partial weight of the creature. The movement assist device assists the creature in periodical walking movement.

According to the movement assist system of the tenth invention, the partial body weight of the creature supported by the load alleviation equipment allows the load on the legs of the creature for maintaining an upstanding state to be alleviated. Accordingly, by using the load alleviation equipment, the continuation of the periodical walking movement of the creature is allowed while maintaining the upstanding state of the foot thereof even in cases where a stepping strength on ground produced to the foot is weak despite that an electrical stimulation is applied to the foot of the creature.

The movement assist system according to an eleventh invention is depended on the movement assist system of the first invention, wherein the movement assist device includes a first orthosis and a second orthosis mounted on a first body part and a second body part of the creature, respectively, as the orthosis, and assists the periodical movement involving a relative periodical movement between the first body part and the second body part by applying to the creature the output from the actuator via the first orthosis and the second orthosis.

According to the movement assist system of the eleventh invention, the second orthosis is moved by operating the actuator of the movement assist device with respect to the first orthosis, thereby, the periodical movement of the second body part relative to the first body part may be assisted.

The movement assist system according to a twelfth invention is depended on the movement assist system of the eleventh invention, wherein the movement assist device is mounted on a third body part of the creature as the orthosis and includes a third orthosis which is connected to actuator with the second orthosis to be present therebetween.

According to the movement assist system of the twelfth invention, the second orthosis is moved by operating the actuator of the movement assist device with respect to the first orthosis, and the third orthosis is moved to follow the movement of the second orthosis. According thereto, in addition to the periodical movement of the second body part relative to the first body part, the movement of the third body part is assisted so as to follow the movement of the second body part.

BRIEF DESCRIPTION OF THE DRAWINGS

FIGS. 5(*a*)-5(*b*) are explanatory diagrams concerning operations of the movement assist device.

FIGS. 6(*a*) to 6(*e*) are explanatory diagrams concerning a timing of an electrical stimulation.

FIG. 7(*b*) is an explanatory diagram of angles of a hip joint.

FIG. 7(*c*) is an explanatory diagram illustrating ON/OFF state of an electrical stimulation.

FIG. 8(*b*) is an explanatory diagram of a determination result on a lifting force with an electrical stimulation being applied.

DETAILED DESCRIPTION OF THE PREFERRED EMBODIMENTS

An embodiment regarding a movement assist system of the present invention will be described with reference to the drawings. Hereinafter, symbols "L" and "R" are used to differentiate a left side and a right side of legs or the like. In cases where there is not necessary to differentiate the left side and the right side or where a vector has both of the left and right components, the symbols are omitted. Moreover, symbols "+" and "−" are used to differentiate a flexion movement (forward movement) and an extension movement (backward movement) of the leg (in particular, the thigh).

Figure 1:
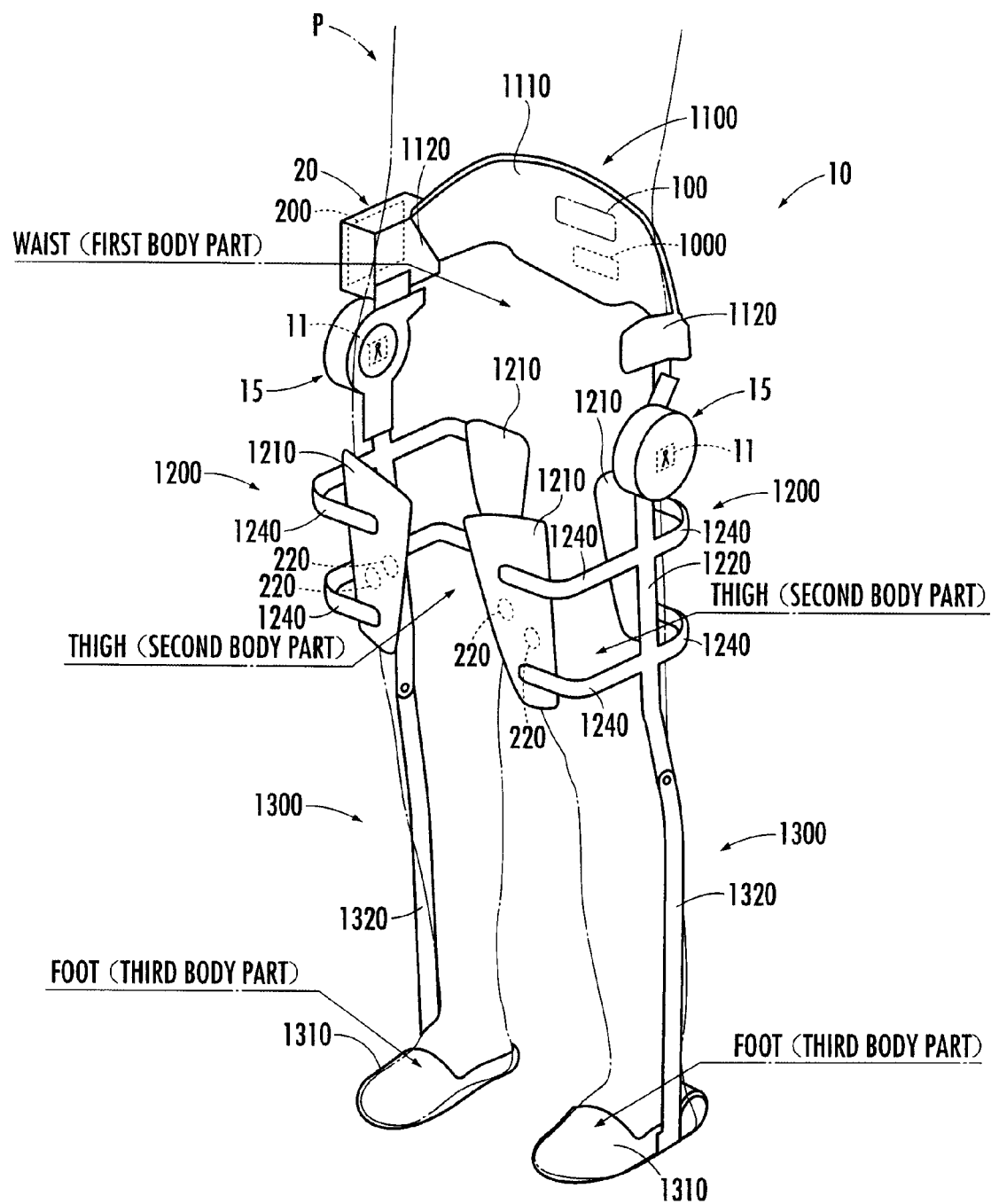
FIG. 1 is an explanatory diagram illustrating a configuration of a movement assist system as a first embodiment of the present invention.

The movement assist system in a first embodiment of the present invention includes a movement assist device 10 and an electrical stimulation device 20, as illustrated in FIG. 1.

FIG. 1 illustrates the movement assist device 10 in the first embodiment of the present invention which assists a human P in walking movement. The movement assist device 10 includes a first orthosis 1100 attached to a waist (a first body part) of the human P, a second orthosis 1200 attached to a thigh (a second body part) of the human P, a third orthosis 1300 attached to a foot (a third part) of the human P, a hip joint angle sensor 11, an actuator 15, a first controller 100, and a battery 1000.

The first orthosis 1100 includes a first supporter 1110 and a first link member 1120. The first supporter 1110 is made from a combination of a rigid material such as rigid resin and a flexible material such as fiber and is mounted backward of the waist. The first link member 1120 is made of rigid resin, and is fixed at the first supporter 1110 in such a way that when the first supporter 1110 is attached to the waist, the first link member 1120 is located at both sides of the waist laterally. The second orthosis 1200 includes a second supporter 1210, a second link member 1220 and a rib member 1240. Similar to the first supporter 1110, the second supporter 1210 is also made from a combination of a rigid material and a flexible material and is mounted on a front side and a back side of the thigh, respectively. The first link member 1120 is made of rigid resin in a way of extending vertically along outside of the thigh and is connected to an output shaft of the actuator 15. The rib member 1240 is made of rigid resin in a way of extending laterally on the front side and back side, respectively, while bending along the thigh. The rib member 1240 is connected to the second supporter 1210. The third orthosis 1300 includes a third supporter 1310, a third link member 1320. The third supporter 1310 is formed to have a shape of a slipper or a shoe which is mounted to a foot of the human P. The third link member 1320 is made of rigid resin in a way of extending vertically along the outside of the lower leg. An upper end of the third link member 1320 is connected to a lower end of the second link member 1220, rotatably around a pitch shaft (a shaft extending in a lateral direction with respect to the human P), and a lower end thereof is movably connected to or fixed at the third supporter 1310. Note that the third orthosis 1300 may be omitted.

The hip joint angle sensor 11 includes a rotary encoder disposed on a transverse side of the waist of the human P and outputs a signal according to the hip joint angle. The actuator 15 is composed of a motor, including either one or both of a reduction gear and a compliance mechanism where appropriate. The battery 1000 is housed in the first orthosis 1100 (for example, fixed in multiple sheets of cloth constituting the first supporter 1110), which supplies electrical power to the actuator 15, the first controller 100 and the like. Note that it is acceptable to attach or house the respective of the first controller 100 and the battery 1000 in the second orthosis 1200 and the third orthosis 1300; it is also acceptable to dispose them separately from the movement assist device 10.

Figure 2:
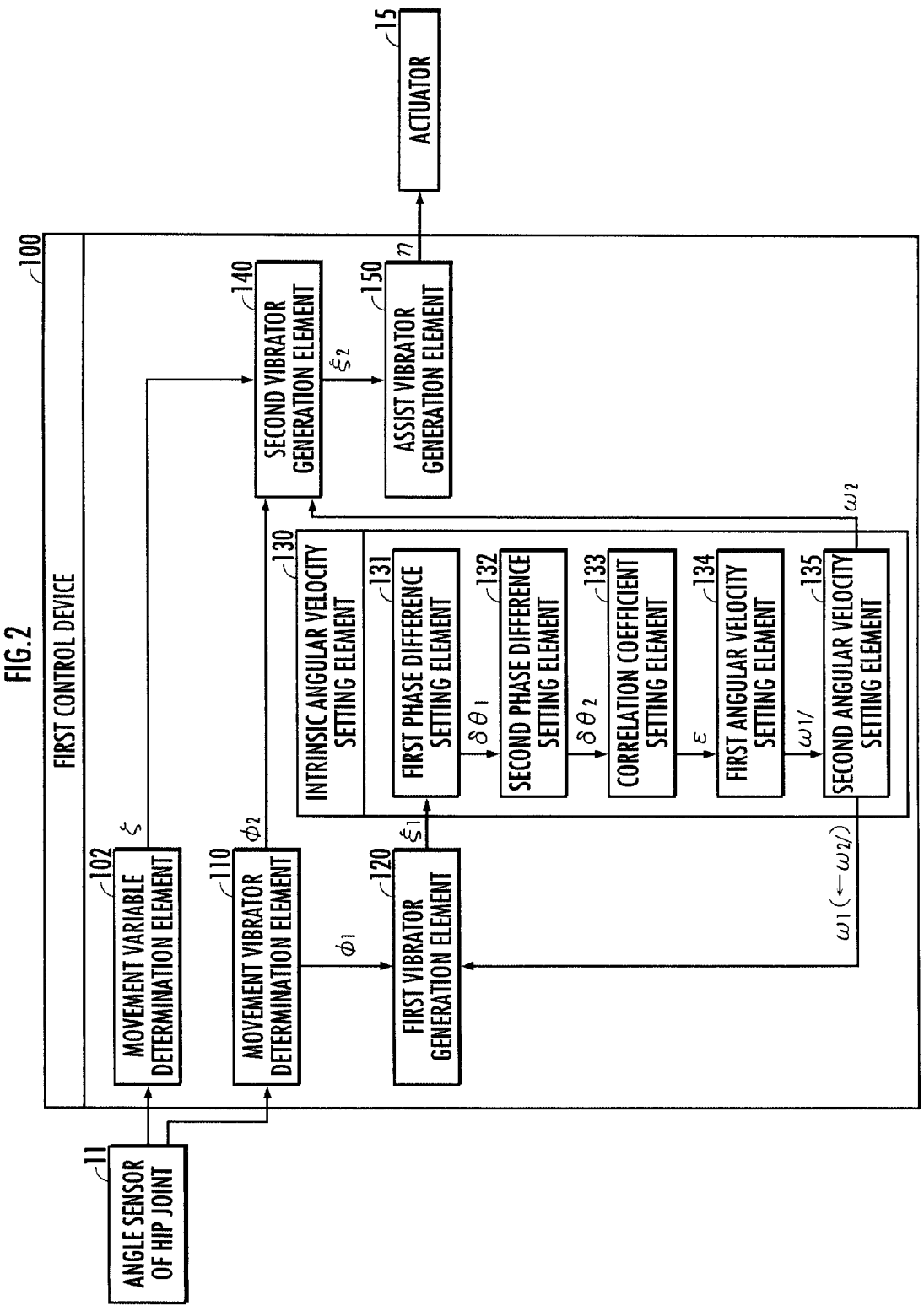
FIG. 2 is an explanatory diagram illustrating a configuration of a controller of the movement assist device in the first embodiment.

The first controller 100 includes a computer housed in the first orthosis 1100 and a program (software) stored in a memory or a storing device in the computer. The first controller 100 controls an operation or an output torque T of the actuator 15 by adjusting an electrical power supplied from the battery 1000 to the actuator 15. The first controller 100 in the first embodiment of the present invention illustrated in FIG. 2 is provided with a movement variable determination element 102, a movement vibrator determination element 110, a first vibrator generation element 120, an intrinsic angular velocity setting element 130, a second vibrator generation element 140, and an assist vibrator generation element 150. Each element may be composed of a mutually different CPU or the like, or a universal CPU or the like.

The movement variable determination element 102 determines a movement variable $\zeta$ which represents the scale of a periodical movement of the human P. The movement vibrator determination element 110 determines an angular velocity of each hip joint as a first movement vibrator $\phi_1$ and an angle of each as a second movement vibrator $\phi_2$, respectively, on the basis of the output from the hip joint angle sensor 11. The first movement vibrator $\phi_1$ and the second movement vibrator $\phi_2$ vary according to the periodical movement of the human P, whose variation pattern is defined according to a magnitude and phase (or an angular velocity which is a first order differentiation of phase by time). Determination of a vibrator refers to the determination of a periodical variation pattern of the vibrator. The first vibrator generation element 120 generates a first vibrator $\xi_1$ as an output vibration signal by inputting the first movement vibrator $\phi_1$ determined by the movement vibrator determination element 110 as an input vibrator signal to a first model. The generation of a vibrator refers to the definition of the periodical variation pattern of the vibrator. The "first model" is a model which generates the output vibration signal varying at a specific angular velocity defined according to a first intrinsic angular velocity $\omega_1$ by entraining to the input vibration signal (synchronization phenomenon).

The intrinsic angular velocity setting element 130 includes a first phase difference setting element 131, a second phase difference setting element 132, a correlation coefficient setting element 133, a first angular velocity setting element 134, and a second angular velocity setting element 135. The intrinsic angular velocity setting element 130 sets a second intrinsic angular velocity $\omega_2$ on the basis of a first phase difference $d\theta_1$ according to a virtual model so as to approximate a second phase difference $d\theta_2$ to a desired phase difference $d\theta_0$. The first phase difference $d\theta_1$ is the phase difference between the first movement vibrator $\phi_1$ determined by the movement vibrator determination element 110 and the first vibrator $\xi_1$ generated by the first vibrator generation element 120. The virtual model is a model which represents the periodical movement of the human P as a periodical variation of a first virtual vibrator $f_1$, the periodical operation of the movement assist device 10 as a periodical variation of a second virtual vibrator $f_2$, and the phase difference between the periodical movement of the human P and the periodical operation of the movement assist device 10 as a phase difference between the first virtual vibrator $f_1$ and the second virtual vibrator $f_2$, respectively.

The second vibrator generation element 140 generates a second vibrator $\xi_2$ as an output vibration signal from a second model by inputting the second movement vibrator $\phi_2$ determined by the movement vibrator determination element 110 as an input vibrator signal to the second model. The "second model" is a model which generates the output vibration signal varying at a specific angular velocity defined according to a second intrinsic angular velocity $\omega_2$ defined by the intrinsic angular velocity setting element 130 on the basis of the input vibration signal.

The assist vibrator generation element 150, on the basis of the second vibrator $\xi_2$, generates an assist vibrator $\eta$ for defining a variation pattern of a torque applied to the thigh by the actuator 15 of the movement assist device 10.

As illustrated in FIG. 1, the electrical stimulation device 20 in the first embodiment includes an electrode 220 and a second controller 200. The electrode 220 is disposed at the thigh (the second body part) where the second orthosis 1200 is mounted, specifically adjacent to quadriceps. Note that it is acceptable to dispose the electrode 220 at an arbitrary location where a physical strength should be produced to the body part of the human P whose body function is degraded due to neuropathy and other diseases. The second controller 200 adjusts the timing of the electrical stimulation applied from the battery 1000 (or another battery different from the battery 1000) to the human P via the electrode 220 on the basis of the partial arithmetic processing result by the first controller 100.

The functions of the movement assist system including the movement assist device 10 and the electrical stimulation device 20 having the respective configuration in the above-mentioned description in the first embodiment of the present invention will be explained. Firstly, a control method of the action of the movement assist device 10 by the first controller 100 will be described.

The movement variable determination element 102, on the basis of the output signal from the hip joint angle sensor 11, determines the left hip joint angle and the right hip joint angle at the respective finished timing of the flexion movement and the finished timing of the extension movement of the thigh for each walking cycle (FIG. 3/S002), in detail the left hip joint angle at the finished timing of the flexion movement, the left hip joint angle at the finished timing of the extension movement, the right hip joint angle at the finished timing of the flexion movement and the right hip joint angle at the finished timing of the extension movement of the thigh, as the movement variable $\zeta=\{\zeta_i|i=L+, L-, R+, R-\}$. Note that it is acceptable to determine a footstep of the human P as the movement variable $\zeta$. The footstep, for example, may be determined on the basis of a correlation among the hip joint angle of the human P which is determined according to the output signal from the hip joint angle sensor 11, the hip joint angle of the human P stored in memory and the feet positions in the anteroposterior direction. Herein, it is possible to determine a step rate (numbers of steps every unit time) and a walking speed of the human P, and thereafter determine the footstep on the basis of the step rate and the walking speed. The step rate may be determined on the basis of an output signal from an acceleration sensor attached to the human P, which outputs the output signal according to an acceleration of the human P in the vertical direction. The walking speed may be determined on the basis of an output signal from a speed sensor disposed in a treadmill 30, which outputs the output signal according to the speed of an endless belt 32. Moreover, it is also acceptable to determine the value of a function, namely the movement variable $\zeta$, having multiple variables containing at least one of the walking rate (=footstep/step rate), the footstep, the left hip joint angle at the finished timing of the flexion movement and the left hip joint angle at the finished timing of the extension movement, the right hip joint angle at the finished timing of the flexion movement and the right hip joint angle at the finished timing of the extension movement of the thigh for each walking cycle.

Figure 3:
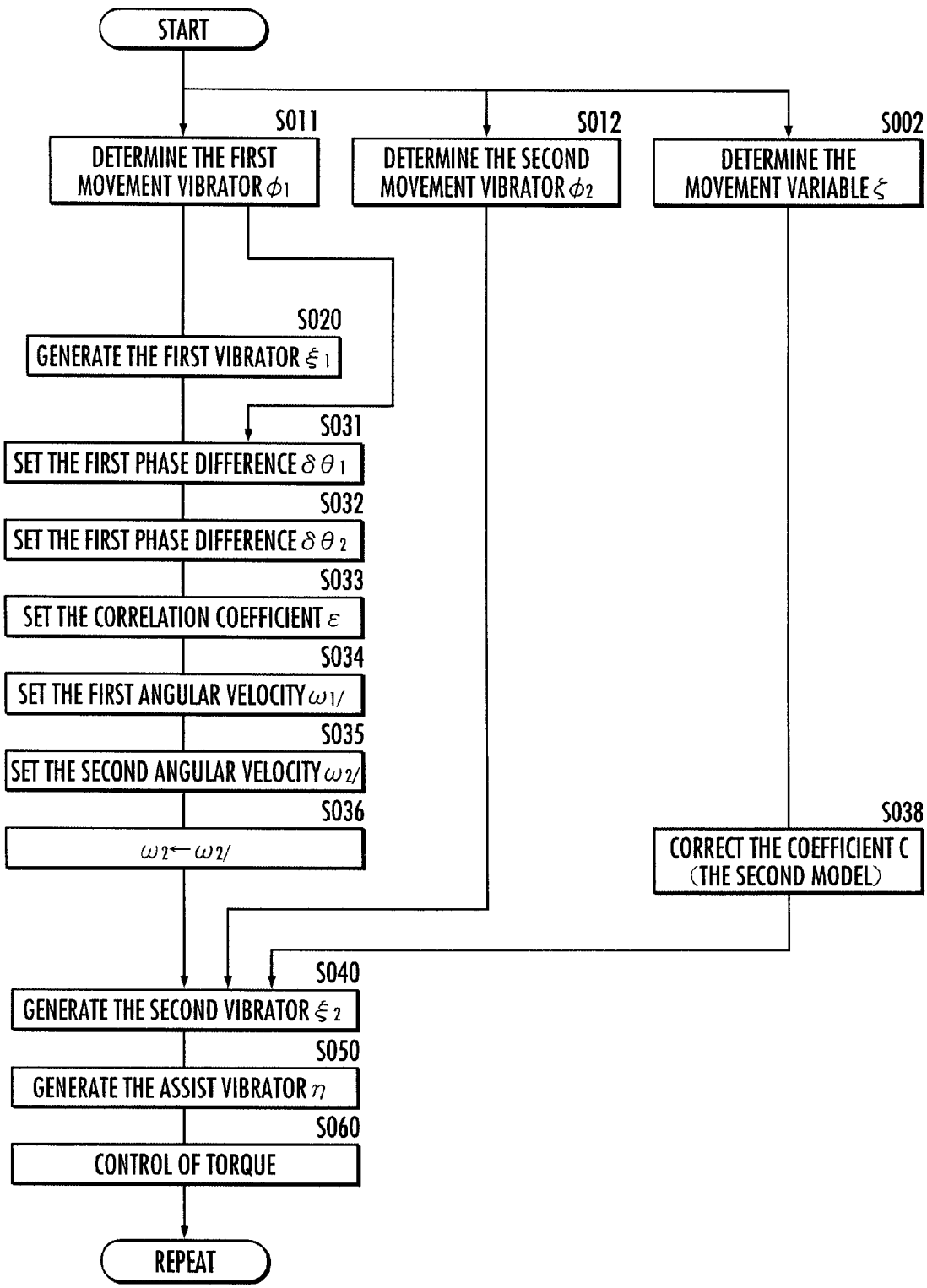
FIG. 3 is an explanatory diagram concerning a movement assist method in the first embodiment.

Further, the movement vibrator determination element 110 determines the angular velocity of each of the left and right hip joints of the human P as the first movement vibrator $\phi_1=(\phi_{1L}, \phi_{1R})$ on the basis of the output from the hip joint angle sensor 11 (FIG. 3/S011). Furthermore, the movement vibrator determination element 110 determines the left hip joint angle and the right joint angle of the human P as the second movement vibrator $\phi_2=(\phi_{2L}, \phi_{2R})$ on the basis of the output from the hip joint angle sensor 11 (FIG. 3/S012).

Note that it is acceptable to determine an arbitrary variable varying periodically according to the periodical movement of the human P by using an appropriate sensor as the first movement vibrator $\phi_1$ and the second movement vibrator $\phi_2$, respectively. For example, the angle or angular velocity of an arbitrary joint, such as the hip joint, knee joint, foot joint, shoulder joint, elbow joint and the like, and the position of the thigh, foot, upper arm and waist (the position or the like in the anteroposterior direction or the vertical direction with the center-of-gravity of the human P as a reference), and the variation patterns of the velocity and acceleration may be determined as the movement vibrator. The variation patterns of various parameters varying at a rhythm in conjunction with the walking locomotor rhythm, such as a sound generated when the left and right feet step on ground, breathing sound, deliberate phonation or the like, may be determined as one or both of the first movement vibrator $\phi_1$ and the second movement vibrator $\phi_2$. Moreover, it is acceptable to determine variables representing the periodical movement state of an identical body part, such as the angle and the angular velocity or the like of an identical joint, as each of the first movement vibrator $\phi_1$ and the second movement vibrator $\phi_2$. It is also acceptable to determine variables representing the periodical movement state of different body parts, such as the respective angles and the angular velocities or the like of different joints, as each of the first movement vibrator $\phi_1$ and the second movement vibrator $\phi_2$.

Thereafter, the first vibrator generation element 120 generates the first vibrator $\xi_1$ as the output vibration signal by inputting the first movement vibrator $\phi_1$ determined by the movement vibrator determination element 110 as the input vibration signal into the first model (FIG. 3/S011). The first model represents the correlation between a plurality of the first elements such as the left and right feet or the like, and generates the output vibration signal which varies at the angular velocity defined according to the first intrinsic angular velocity $\omega_1=(\omega_{1L}, \omega_{1R})$ by entraining to the input vibration signal as described above. The first model, for example, may be defined by the Van der Pol equation expressed by the equation (10). Moreover, it is possible that the first vibrator generation element 120 sequentially updates the first model by adopting a new second intrinsic angular velocity $\omega_2$ set by the intrinsic angular velocity setting element 130 as a new first intrinsic angular velocity $\omega_1$, and generates a subsequent first vibrator $\xi_1$ as the output vibration signal by inputting a subsequent first movement vibrator $\phi_1$ as the input vibration signal into the new first model.

$$(d^2\phi_{1L}/dt^2)=A(1-\xi_{1L}^2)(d\xi_{1L}/dt)-\omega_{1L}^2\xi_{1L}+g(\xi_{1L}-\xi_{1R})+K_1\phi_{1L},$$

$$(d^2\phi_{1R}/dt^2)=A(1-\xi_{1R}^2)(d\xi_{1R}/dt)-\omega_{1R}^2\xi_{1R}+g(\xi_{1R}-\xi_{1L})+K_1\phi_{1R} \quad (10)$$

wherein:

A: a positive coefficient set in such a way that a stable limit cycle may be drawn from the first vibrator $\xi_1$ and the first order temporal differentiation value $(d\xi_1/dt)$ thereof in a plane of "$\xi_1-(d\xi_1/dt)$";

g: a first correlation coefficient for reflecting the correlation of different body parts such as the left and right feet of the human P or the like to the correlation of each of the left and right components of the first vibrator $\xi_1$ (correlation of the output vibration signals among the plurality of the first elements); and $K_1$: a feedback coefficient with respect to the first movement vibrator $\phi_1$.

The first vibrator $\xi_1=(\xi_{1L}, \xi_{1R})$ is calculated or generated according to the Runge-Kutta method. The respective angular velocity of the components $\xi_{1L}$ and $\xi_{1R}$ of the first vibrator $\xi_1$ represents a virtual rhythm which assists the respective movement of the left foot and the right foot. Further, the first vibrator $\xi_1$ has the property to vary or vibrate periodically with an autonomous angular velocity or rhythm defined on the basis of the first intrinsic angular velocity $\omega_1$ while harmonizing with the rhythm of the first movement vibrator $\phi_1$ varying at an angular velocity or rhythm substantially the same as a rhythm of the actual walking movement, according to the "mutual entrainment" (harmonization effect) which is one of the properties of the Van del Pol equation.

In addition, the first model may be expressed by the Van der Pol equation having a form different from that of the equation (10), or by a certain equation which generates the output vibration signal varying periodically at the angular velocity defined on the basis of the first intrinsic angular velocity $\omega_1$, accompanied by the mutual entrainment to the input vibration signal. Moreover, it is acceptable to increase the numbers of the first movement vibrator $\phi_1$, namely the determination object. The more numbers of the first movement vibrators $\phi_1$ are input to the first model, the movement will be more elaborately assisted by considering the movements of various body parts of the human P through the adjustment of the correlation coefficients, although the correlation members in a non-linear differentiation equation corresponding to the generation of the first vibrator $\xi_1$ in the Van der Pol equation for defining the first model will become more accordingly.

The phase difference between the periodical movement of the human P and the periodical motion of the movement assist device 10 specifies the moving behavior of the human P with respect to the motion of the movement assist device 10. For example, in cases where the phase difference is positive, the human P moves in a way of leading the movement assist device 10. On the other hand, in cases where the phase difference is negative, the human P moves in a way of being led by the movement assist device 10. Therefore, the deviation of the phase difference (the first phase difference) $d\theta_1$ of the first vibrator $\xi_1$ with respect to the first movement vibrator $\phi_1$ from the desired phase difference $d\theta_0$ will make unstable the moving behavior of the human P. Consequently, there is a high probability that the locomotor rhythm of the human P whose relative movements between the waist and the thigh assisted by the torque T varying periodically at an angular velocity corresponding to the assist vibrator η would deviate from the desired locomotor rhythm.

Therefore, from the viewpoint of matching the locomotor rhythm of the human P with the desired locomotor rhythm while maintaining the mutual harmonic content between the first movement vibrator $\phi_1$ and the first vibrator $\xi_1$, the second intrinsic angular velocity $\omega_2$ appropriate for defining the second vibrator $\xi_2$ is set by the intrinsic angular velocity setting element 130. In other words, an appropriate second intrinsic angular velocity $\omega_2$ is set from the viewpoint of maintaining an appropriate phase difference between an assist rhythm of the movement assist device 10 and the locomotor rhythm of the human P so that the locomotor rhythm of the human P is in accordance with the assist rhythm of the movement assist device 10 while harmonizing the assisting rhythm of the movement assist device 10 with the locomotor rhythm of the human P.

Specifically, the first phase difference setting element 131 sets a phase difference between the first movement vibrator $\phi_1$ and the first vibrator $\xi_1$ as the first phase difference $d\theta_1$ (FIG. 3/S031). The first phase difference $d\theta_1$ is calculated or set on the basis of a difference of time between, for example, a time where $f_1=0$ and $(df_1/dt)>0$ and a time where $\xi_1=0$ and $(d\xi_1/dt)>0$.

Thereafter, the second phase difference setting element 132 sets the second phase difference $d\theta_2$ on a condition that the first phase difference $d\theta_1$ over the recent three walking cycles is constant or the variation of the first phase difference $d\theta_1$ is within an allowable range (FIG. 3/S032). In detail, a phase difference between the first virtual vibrator $f_1$ and the second virtual vibrator $f_2$ which are defined in the virtual model, which is represented by the equations (21) and (22), is set as the second phase difference $d\theta_2$ according to the equation (23). The first virtual vibrator $f_1$ in the virtual model virtually represents the first movement vibrator $\phi_1$; the second virtual vibrator $f_2$ in the virtual model represents the assist vibrator η virtually.

$$d\phi_{1L}/dt=\omega_{1L}+\epsilon_L \sin(\phi_{2L}-\phi_{1L}), d\phi_{1R}/dt=\omega_{1R}+\epsilon_R \sin(\phi_{2R}-\phi_{1R}) \quad (21)$$

$$d\phi_{2L}/dt=\omega_{2L}+\epsilon_L \sin(\phi_{1L}-\phi_{2L}), d\phi_{2R}/dt=\omega_{2R}+\epsilon_R \sin(\phi_{1R}-\phi_{2R}) \quad (22)$$

$$\delta\theta_{2L}=\arcsin\{(\omega_{1/L}-\omega_{2/L})2\epsilon_L\}, \delta\theta_{2R}=\arcsin\{(\omega_{1/R}-\omega_{2/R})/2\epsilon_R\} \quad (23)$$

Wherein, each component of "$e=(e_L, e_R)$" stands for a correlation coefficient representing the correlation between each component of the first virtual vibrator $f_1$ and each component of the second virtual vibrator $f_2$. "$\omega_{1/}=(\omega_{1/L}, \omega_{1/R})$" is the angular velocity for each component of the first virtual vibrator $f_1$, and "$\omega_{2/}=(\omega_{2/L}, \omega_{2/R})$" is the angular velocity for each component of the second virtual vibrator $f_2$.

Subsequently, the correlation coefficient setting element 133 sets the correlation coefficient e so that the deviation between the first phase difference $d\theta_1$ set by the first phase difference setting element 131 and the second phase difference $d\theta_2$ set by the second phase difference setting element 132 is minimum (FIG. 3/S033).

Specifically, the correlation coefficient $e(t_i)$ at each time $t_k$ where the first movement vibrator $\phi_1$ for each of the left and right components becomes zero is sequentially set according to the equation (24).

$$\epsilon_L(t_{k+1})=\epsilon_L(t_k)-B_L\{V_{1L}(t_{k+1})-V_{1L}(t_k)\}/\{\xi_L(t_k)-\epsilon_L(t_{k-1})\},$$

$$\epsilon_R(t_{k+1})=\epsilon_R(t_k)-B_R\{V_{1R}(t_{k+1})-V_{1R}(t_k)\}/\{\epsilon_R(t_k)-\epsilon_R(t_{k-1})\},$$

$$V_{1L}(t_{k+1})=(1/2)\{\delta\theta_{1L}(t_{k+1})-\delta\theta_{2L}(t_k)\}^2,$$

$$V_{1R}(t_{k+1})=(1/2)\{\delta\theta_{1R}(t_{k+1})-\delta\theta_{2R}(t_k)\}^2 \quad (24)$$

Wherein, each component of "$B=(B_L, B_R)$" stands for a coefficient representing the stability of the potential $V_1=(V_{1L}, V_{1R})$ for approximating each component of the first phase difference $d\theta_1$ to each of the left and right components of the second phase difference $d\theta_2$.

Next, the first angular velocity setting element 134 sets the angular velocity of the first virtual vibrator $f_1$ as the first angular velocity $\omega_{1/}$ according to the equation (25) on the basis of the correlation coefficient e set by the correlation coefficient setting element 133 so that the deviation between the first phase difference $d\theta1$ and the second phase difference $d\theta_2$ for each component is minimum at the condition that the angular velocity $\omega_{2/}$ of the first virtual vibrator $f_2$ is constant (FIG. 3/S034).

$$\omega_{1/L}(t_k) = -\alpha_L \int dt q_{1L}(t),$$

$$\omega_{1/R}(t_k) = -\alpha_R \int dt q_{1R}(t)$$

$$q_{1L}(t) = (4\varepsilon_L^2(t_k) - (\omega_{1L}(t) - \omega_{2L}(t_k)))^{1/2} \times$$
$$\sin(\arcsin[(\omega_{1/L}(t) - \omega_{2/L}(t_{k-1}))/2\varepsilon_L(t_k)] - \delta\theta_{2L}(t_k)),$$

$$q_{1R}(t) = (4\varepsilon_R^2(t_k) - (\omega_{1/R}(t) - \omega_{2/R}(t_k)))^{1/2} \times$$
$$\sin(\arcsin[(\omega_{1/R}(t) - \omega_{2/R}(t_{k-1}))/2\varepsilon_R(t_k)] - \delta\theta_{2R}(t_k)) \quad (25)$$

wherein, each component of "$a=(a_L, a_R)$" stands for the coefficient representing the stability of the system.

The virtual model is constructed on a condition that the mutual harmonic content between the first movement vibrator $\phi_1$ and the first vibrator $\xi_1$ is also maintained between the first virtual vibrator $f_1$ and the second virtual vibrator $f_2$ by setting the correlation coefficient e and the angular velocity $\omega_{1/}$. In other words, the virtual model is constructed so that the first virtual vibrator $f_1$ representing the periodical movement of the human P and the second virtual vibrator $f_2$ representing the periodical motion of the movement assist device 10 vary periodically at the second phase difference $d\theta_2$ with a mutual harmonization.

Thereafter, the second angular velocity setting element 135 set the angular velocity of the first virtual vibrator $f_2$ as the second angular velocity $\omega_{2/}$ for each component on the basis of the first angular velocity $\omega_{1/}$ set by the first angular velocity setting element 134 (FIG. 3/S035). The second angular velocity $\omega_2 = (\omega_{2/L}, \omega_{2/R})$ is set according to the equation (26) so that the second phase difference $d\theta_2$ for each of the left and right components approximates to the desired phase difference $d\theta_0$. Subsequently, the second angular velocity $\omega_{2/}$ is set as the second intrinsic angular velocity 2 (FIG. 3/S036).

$$\omega_{2/L}(t_k) = \beta_L \int dt q_{2L}(t),$$

$$\omega_{2/R}(t_k) = \beta_R \int dt q_{2R}(t)$$

$$q_{2L}(t) = (4\varepsilon_L^2(t_k) - (\omega_{1/L}(t) - \omega_{2/L}(t_k)))^{1/2} \times$$
$$\sin(\arcsin[(\omega_{1/L}(t_k) - \omega_{2/L}(t_k))/2\varepsilon_L(t_k)] - \delta\theta_0),$$

$$q_{2R}(t) = (4\varepsilon_R^2(t_k) - (\omega_{1/R}(t) - \omega_{2/R}(t_k)))^{1/2} \times$$
$$\sin(\arcsin[(\omega_{1/R}(t_k) - \omega_{2/R}(t))/2\varepsilon_R(t_k)] - \delta\theta_0)$$

(26)

Wherein, each component of "$\beta=(\beta_L, \beta_R)$" stands for the coefficient representing the stability of the system.

Accordingly, the second angular velocity $\omega_{2/}$ is appropriately set from the viewpoint of approximating the phase difference between the periodical movement of the human P represented by the first virtual vibrator $f_1$ and the periodical motion of the movement assist device 10 represented by the first virtual vibrator $f_2$ to the desired phase difference $d\theta_0$, while the mutual harmonic content between the first movement vibrator $\phi_1$ and the first vibrator $\xi_1$ is maintained between the periodical movement of the human P and the periodical motion of the movement assist device 10.

The second vibrator generation element 140 corrects a second model by appropriately correcting a coefficient c contained in simultaneous differentiation equations which represent the second model according to the equation (28) (FIG. 3/S038). "$c=\{c_i|i=L+, L-, R+, R-\}$" is a coefficient to be adjusted so that the movement variable $\zeta$ determined by the movement variable determination element 102 approximates to a desired value $\zeta_0$ or a deviation therebetween becomes minimum.

$$c_i(t_{k+1})=c_i(t_k)-C_i\{V_i(t_{k+1})-V_i(t_k)\}/\{c_i(t_K)-c_i(t_{k-1})\},$$

$$V_i(t_{k+1})\equiv(\frac{1}{2})\{\xi_i(t_{k+1})-\xi_i(t_k)\}^2 \quad (28)$$

Each component of "$c=C_{L+}, C_{L-}, C_{R+}, C_{R-}$" stands for the coefficient representing the stability of a potential $V_2=(V_{2L+}, V_{2L-}, V_{2R+}, V_{2R-})$ for approximating each component of the determination values of the movement variable $\zeta$ to each component of the desired value $\zeta_0$ thereof. "$\zeta_0=\{\zeta_{0i}|i=L+, L-, R+, R-\}$" stands for the desired value for each of the left hip joint angle and the right hip joint angle at the finished time of the flexion movement and the extension movement of the thigh every walking cycle, respectively. This desired value $\zeta_0$ may be calculated on the basis of the desired footstep of the human P which is stored preliminarily in the memory, according to the correlation between the left hip joint angle and the right hip joint angle and footstep between the left and right feet at the finished time of the flexion movement and the extension movement of the thigh every walking cycle, respectively, which are stored preliminarily in the memory.

Thereafter, the second vibrator generation element 140 generates the second vibrator $\xi_2=(\xi_{2L+}, \xi_{2L-}, \xi_{2R+}, \xi_{2R-})$ as an output vibration signal, by inputting to the second model the second movement vibrator $\phi_2$ determined by the movement vibrator determination element 110 as an input signal (FIG. 3/S040). The second model is a model representing the correlation between a plurality of second elements including the neural elements or the like responsible for the movements to the flexion direction (forward direction) and the extension direction (backward direction) of each leg, generating the output signal varying at an angular velocity defined according to the second intrinsic angular velocity $\omega_2$ set by the intrinsic angular velocity setting element 130 on the basis of the input signal as aforementioned.

The second model is defined by the simultaneous differentiation equations represented by, for example, the equation (30). The simultaneous differentiation equations contain therein a state variable $u=\{u_i|i=L+, L-, R+, R-\}$ representing the behavior state (specified by amplitude and phase) to each of the flexion direction (forward direction) and the extension direction (backward direction) of each thigh, and a self-inhibition factor $v=\{v_i|i=L+, L-, R+, R-\}$ for representing compliance of each behavior state. Moreover, the simultaneous differentiation equations contain therein the desired value $\zeta_0$ for each of the left hip joint angle and the right hip joint angle at the finished time of the flexion movement and the extension movement of the thigh every walking cycle, respectively, and the coefficient c for correcting the second model as mentioned above. Moreover, it is acceptable to increase the numbers of the second movement vibrator $\phi_2$, namely the determination object. The more numbers of the second movement vibrators $\phi_2$ are input to the second model, the more the correlation members in the simultaneous differentiation equations will become, however, it may allow an appropriate assist in the periodical movement of the human P by considering the correlation between movement states of various body parts of the human P through the adjustment of the correlation coefficients.

$$\tau_{1L+}(du_{L+}/dt)=c_{L+}\zeta_{0L+}-u_{L+}+w_{L+/L-}\xi_{2L-}+w_{L+/R+}\xi_{2R+}-\lambda_L v_{L+}+f_1(\omega_{2L})+f_2(\omega_{2L})K_2\phi_{2L},$$

$$\tau_{1L-}(du_{L-}/dt)=c_{L-}\zeta_{0L-}-u_{L-}+w_{L-/L+}\xi_{2L+}+w_{L-/R-}\xi_{2R-}-\lambda_L v_{L-}+f_1(\omega_{2L})+f_2(\omega_{2L})K_2\phi_{2L},$$

$$\tau_{1R+}(du_{R+}/dt)=c_{R+}\zeta_{0R+}-u_{R+}+w_{R+/L+}\xi_{2L+}+w_{R+/R-}\xi_{2R-}-\lambda_R v_{R+}+f_1(\omega_{2R})+f_2(\omega_{2R})K_2\phi_{2R},$$

$$\tau_{1R-}(du_{R-}/dt)=c_{R-}\zeta_{0R-}-u_{R-}+w_{R-/L-}\xi_{2L-}+w_{R-/R+}\xi_{2R+}-\lambda_R v_{L+}+f_1(\omega_{2R})+f_2(\omega_{2R})K_2\phi_{2R},$$

$$\tau_{2i}(dv_i/dt)=-v_i+\xi_{2i},$$

$$\xi_{2i}=H(u_i-u_{th})=0(u_i<u_{thi}) \text{ or } u_i(u_{i\geq uhi}, \text{ or}$$

$$\xi_{2i}=fs(u_i)=u_i/(1+\exp(-u_i/D)) \quad (30)$$

"$t_{1i}$" is a time constant for defining the variation feature of the state variable $u_i$, which is represented by the equation (31) using a $\omega$-dependant coefficient $t_{(\omega)}$ and a constant $\gamma=(\gamma_L, \gamma_R)$. The time constant varies in dependence on the second intrinsic angular velocity $\omega_2$.

$$\tau_{1i}=(t(\omega_{2L})/\omega_{2L})-\gamma_L(i=L+,L-), (t(\omega_{2R})/\omega_{2R})-\gamma_R(i=R+, R-) \quad (31)$$

"$t_{2i}$" is a time constant for defining the variation feature of the self-inhibition factor $v_i$. "$w_{i/j}$" is a negative second correlation coefficient e for representing the correlation between the state variables $u_i$ and $u_j$ which represent the movements of the left and right legs of the human P toward the flexion direction and the extension direction as the correlation of each component of the second vibrator $\xi_2$ (correlation between the output vibration signals of the plurality of the second elements). "$\lambda_L$" and "$\lambda_R$" are compliant coefficients. "$K_2$" is a feedback coefficient in correspondence to the second movement vibrator $\phi_2$.

"$f_1$" is a first order function of the second intrinsic angular velocity $\omega_2$ defined according to the equation (32) by using the positive coefficient c. "$f_2$" is a second order function of the second intrinsic angular velocity $\omega_2$ defined according to the equation (33) by using the coefficients $c_0$, $c_1$ and $c_2$.

$$f_1(\omega) \equiv c\omega \tag{32}$$

$$f_2(\omega) \equiv c_0 + c_1\omega + c_2\omega^2 \tag{33}$$

The second vibrator $\xi_{2i}$ equals to zero when the value of the state variable $u_i$ is smaller than a threshold value $u_{th}$; and equals to the value of $u_i$ when the value of the state variable $u_i$ is not smaller than the threshold value $u_{th}$. In other words, the second vibrator $\xi_{2i}$ is defined by a sigmoid function fs (refer to equation (30)). According thereto, if the state variable $u_{L+}$ representing the behavior of the left thigh toward the forward side increases, the amplitude of the left flexion component $\xi_{2L+}$ of the second vibrator $\xi_2$ becomes greater than that of the left extension component $\xi_{2L-}$; if the state variable $u_{R+}$ representing the behavior of the left thigh toward the forward side increases, the amplitude of the left flexion component $\xi_{2R+}$ of the second vibrator $\xi_2$ becomes greater than that of the left extension component $\xi_{2R-}$. Further, if the state variable $u_{L-}$ representing the behavior of the left thigh toward the backward side increases, the amplitude of the left extension component $\xi_{2L-}$ of the second vibrator $\xi_2$ becomes greater than that of the left flexion component $\xi_{2L+}$; if the state variable $u_{R-}$ representing the behavior of the left thigh toward the backward side increases, the amplitude of the left extension component $\xi_{2R-}$ of the second vibrator $\xi_2$ becomes greater than that of the left flexion component $\xi_{2R+}$. The movement toward the forward or backward direction of the leg (thigh), is recognized by, for example, the polarity of the hip joint angular velocity.

Next, the assist vibrator generation element 150 sets the assist vibrator $\eta = (\eta_L, \eta_L)$ on the basis of the second vibrator $\xi_2$ generated by the second vibrator generation element 140 (FIG. 3/S050). Specifically, the assist vibrator $\eta$ is generated according to the equation (40). In other words, the left component $\eta_L$ of the assist vibrator $\eta$ is calculated as a sum of a product of the left flexion component $\xi_{2L+}$ of the second vibrator $\xi_2$ and the coefficient $\chi_{L+}$, and a product of the left extension component $\xi_{2L-}$ of the second vibrator $\xi_2$ and the coefficient "$-\chi_{L-}$". The right component $\eta_R$ of the assist vibrator $\eta$ is calculated as a sum of a product of the right flexion component $\xi_{2R+}$ of the second vibrator $\xi_2$ and the coefficient $\chi_{R+}$, and a product of the right extension component $\xi_{2L-}$ of the second vibrator $\xi_2$ and the coefficient "$-\chi_{R-}$".

$$\eta_L = \chi_{L+}\xi_{2L+} - \chi_{L-}\xi_{2L-}, \eta_R = \chi_{R+}\xi_{2R+} - \chi_{R-}\xi_{2R-} \tag{40}$$

Thereafter, a current $I=(I_L, I_R)$ supplied to each of the left and right actuators 15 from the battery 1000 is adjusted by the first controller 100 on the basis of the assist vibrator $\eta$. The current I is represented by, for example, $I(t)=G_1*\eta(t)$ (wherein, $G_1$ is a ratio coefficient) on the basis of the assist vibrator $\eta$. Thereby, the force for moving each thigh (the second body part) with respect to the waist (the first body part) or the torque $T=(T_L, T_R)$ around the hip joint, which is applied to the human P from the movement assist device 10 via the first orthosis 1100 and the second orthosis 1200, is adjusted (FIG. 3/S060). The torque T is represented by, for example, $T(t)=G_2*I(t)$ (wherein, $G_2$ is a ratio coefficient) on the basis of the current I. Thereafter, the series of the aforementioned processes are performed repeatedly. Note that it is acceptable to control the motion of the movement assist device 10 irrelative to the aforementioned control method on the condition that the thigh is appropriately moved with respect to the waist in a duration from the initiation of the walking movement of the human P to the finish of 2-3 steps of the walking movement.

Hereinafter, a control method of the electrical stimulation device 20 by the second controller 200 in the first embodiment of the present invention will be explained. The second controller 200 receives sequentially an output signal from the first controller 100 and adjusts the timing of the electrical stimulation applied to the leg of the human P from the battery 1000 via the electrode 220. The output signal represents the value of the state variable $u_i$ which is calculated in the generation process of the second vibrator $\xi_2$ by the second vibrator generation element 140.

Figure 4:
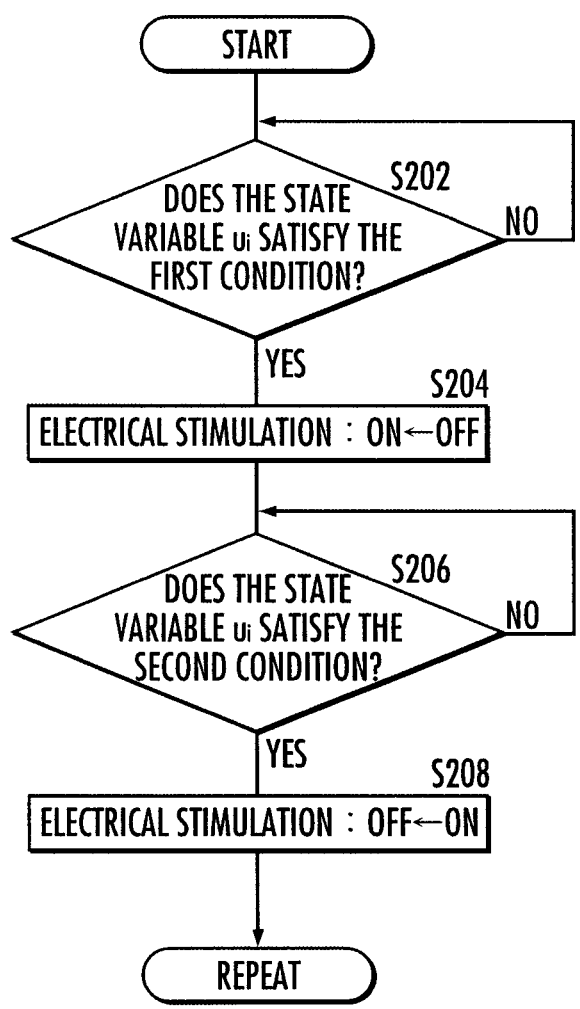
FIG. 4 is an explanatory diagram concerning an adjusting method of an electrical stimulation.

With respect to each thigh, whether the value of the state variable $u_i$ calculated according to the arithmetic processing result of the second vibrator generation element 140 satisfies a first condition is determined (FIG. 4/S202). With respect to the right thigh, the first condition is set when the deviation $du_R=u_{R+}-u_R$ between the state variables $u_{R+}$ and $u_{R-}$ which represent the movement state of the right thigh is equal to or greater than a first right threshold $u_{1R}$ and a first order differentiation value thereof ($ddu_R/dt$) is positive. With respect to the left thigh, the first condition is set when the deviation $du_L=u_{L+}-u_{L-}$ between the state variables $u_{L+}$ and $u_{L-}$ which represent the movement state of the left thigh is equal to or greater than a first left threshold $u_{1L}$ and a first order differentiation value ($ddu_L/dt$) thereof is positive.

In cases where the state variable $u_i$ is determined to meet the first condition (YES in FIG. 4/S202), the electrical stimulation is applied to the thigh (FIG. 4/S204). It is acceptable to control the strength of the electrical stimulation applied to each thigh on the basis of the corresponding deviation $du_R$ and $du_L$, respectively.

Subsequently, with respect to each thigh, whether the value of the state variable $u_i$ calculated according to the arithmetic processing result of the second vibrator generation element 140 satisfies a second condition is determined (FIG. 4/S206). With respect to the right thigh, the second condition is set when the deviation $du_R=u_{R+}-u_{R-}$ between the state variables $u_{R+}$ and $u_{R-}$ which represent the movement state of the right thigh is equal to or greater than a second right threshold $u_{2R}$ and a first order differentiation value thereof ($ddu_R/dt$) is positive. With respect to the left thigh, the second condition is set when the deviation $du_L=u_{L+}-u_{L-}$ between the state variables $u_{L+}$ and $u_{L-}$ which represent the movement state of the left thigh is equal to or greater than a second left threshold $u_{2L}$ and a first order differentiation value thereof ($ddu_L/dt$) is positive.

In cases where the state variable $u_i$ is determined not to meet the second condition (NO in FIG. 4/S206), the electrical stimulation applied to the thigh is continued (FIG. 4/S204). On the other hand, in cases where the state variable $u_i$ is determined to meet the second condition (YES in FIG. 4/S206), the electrical stimulation applied to the thigh is stopped (FIG. 4/S208). Thereafter, the series of the aforementioned processes are performed repeatedly.

According to the movement assist system in the first embodiment of the present invention which performs the aforementioned functions, the second orthosis 1200 is moved by the actuator 15 with respect to the first orthosis 1100, as illustrated in FIGS. 5(a) and 5(b), and the third orthosis 1300 is moved to follow the movement of the second orthosis 1200. Consequently, in addition to the period movement of the thigh (the second body part) being assisted with respect to the waist (the first body part), the lower leg (the third body part) is assisted so as to follow the thigh in movement. As a result, the periodical walking movement of the human P is assisted so that the scale and rhythm of the walking movement matches the desired scale and the desired rhythm thereof, respectively.

Specifically, the movement of the human P is assisted by the movement assist device 10 so that the movement rhythm of the human P matches the desired movement rhythm according to the following reasons. In other words, as mentioned in the above, the second intrinsic angular velocity $\omega_2$ is set appropriately from the viewpoint of approximating the phase difference between the periodical movement of the human P represented by the first virtual vibrator $f_1$ and the periodical motion of the movement assist device 10 represented by the first virtual vibrator $f_2$ to the desired phase difference $d\theta_0$, while the mutual harmonic content between the first movement vibrator $\phi_1$ and the first vibrator $\xi_1$ is maintained between the periodical movement of the human P and the periodical motion of the movement assist device 10 (FIG. 3/S031-S036). Thereby, the output torque T, which is controlled on the basis of the second vibrator $\xi_2$ varying periodically at the angular velocity defined on the basis of the second intrinsic angular velocity $\omega_2$, varies periodically at the angular velocity defined on the basis of the second intrinsic angular velocity $\omega_2$. According thereto, by applying the torque T to the human P, the movement rhythm of the human P and the motion rhythm of the movement assist device 10 is harmonized, and the periodical walking movement of the human P is assisted so as to match the movement rhythm of the human P with the desired movement rhythm.

Moreover, the movement of the human P is assisted so that the movement scale of the human P matches the desired movement scale according to the following reasons. In other words, the second model is corrected so as to approximate the value of the movement variable $\zeta$ representing the movement scale of the periodical walking movement of the human P to the desired value $\zeta_0$ (refer to FIG. 3/S038). Herein, the movement variable $\zeta$ refers to the left hip joint angle and the right hip joint angle at the finished time of the flexion movement and the extension movement of the thigh, respectively, in each walking cycle. Thereafter, the second vibrator $\xi_2$ is generated according to the corrected second model and the torque T applied to the human P is controlled on the basis of the second vibrator $\xi_2$ (refer to FIG. 3/S050 and S060). Resultantly, in spite of the rhythm speed of the periodical movement of the human P, the periodical movement can be assisted by applying a force with an appropriate strength to the human P so as to make the movement scale (the footstep, the maximum hip joint angle or the like) thereof match the desired movement scale.

The electrical stimulation applied to the human P is adjusted by the second controller 200 on the basis of the output signal representing the arithmetic processing result of the first controller 100. The arithmetic processing result of the first controller 100 is the primary determination factor of the output of the actuator 15 which is the control object thereof and the periodical movement state of the human P which is assisted by the output of the actuator 15. Accordingly, it is possible to apply an electrical stimulation to the human P at an appropriate timing and magnitude from the viewpoint of maintaining an appropriate posture by considering the periodical movement state of the human P even in cases where the body function of the human P is degraded due to neuropathy or the like.

In detail, at a timing where the state variable $u_i$ of the right leg is determined to meet the first condition ($du_R = u_{R+} - u_{R-} = u_{1R}$, $ddu_R/dt > 0$), the electrical stimulation is applied to the right leg (refer to YES in S202 and S204 in FIG. 4). In cases where the state variable $u_i$ meets the first condition, the state variable $u_{R+}$ representing the forward movement state of the right leg is in a increasing state and the contribution degree of the second vibrator $\xi_{2R+}$ to the assist vibrator $\eta$ is greater, it is estimated that there is a high probability that the right leg is moved forward (refer to equations (30) and (40)). In other words, the right leg in this case is estimated to be in a situation where the right leg leaving the ground as illustrated in FIG. 6(a) is located front of the basic frontal plane and immediately before stepping on the ground. Therefore, at the time when the human P has the right leg leaving the ground in a state immediately before stepping on the ground and a physical strength to the right leg is necessary in order to maintain the posture after the leg steps on the ground are estimated, the electrical stimulation is applied to the right leg.

Further, at a timing where the state variable $u_i$ of the right leg is determined not to meet the second condition ($du_R = u_{R+} - u_{R-} = u_{2R}$, $ddu_R/dt < 0$), the electrical stimulation is applied to the right leg continuously (refer to NO in S206 of FIG. 4). In cases where the state variable $u_i$ does not meet the second condition, the state variable $u_{R-}$ representing the backward movement state of the right leg is in a increasing state, the contribution degree of the second vibrator $\xi_{2R-}$ to the assist vibrator $\eta$ is smaller, it is estimated that there is a high probability that the right leg stepped on the ground is only moved backward slightly (refer to equations (30) and (40)). In other words, the right leg in this case is estimated to be stepping on the ground as illustrated in FIGS. 6(b) and 6(c). Therefore, during the period when the human P has the right leg leaving the ground stepped on the ground and a physical strength to the right leg is necessary in order to maintain the upstanding posture are estimated, the electrical stimulation continues to be applied to the right leg.

In cases where the state variable $u_i$ of the right leg is determined to meet the second condition, the electrical stimulation being applied to the right leg is stopped (refer to YES in S206 and S208 of FIG. 4). In cases where the state variable $u_i$ of the right leg meets the second condition, the state variable $u_{R-}$ representing the backward movement state of the right leg increases and the contribution degree of the second vibrator $\xi_{2R-}$ to the assist vibrator $\eta$ is greater, it is estimated that there is a high probability that the thigh on ground is moved sufficiently backward. In other words, in this case, it is estimated that the right leg of the human P illustrated in FIGS. 6(d) and 6(e) is located back of the basic frontal plane and is about to leave the ground or is leaving the ground. Accordingly, at the time when the right leg of the human P is about to leave the ground and the strength of the right leg, although weak, may be sufficient to maintain the posture thereof are estimated, the electrical stimulation applied to the right leg is stopped.

Therefore, even in the case where the partial body such as the leg or the like of the human P can not be moved normally duo to neuropathy, the electrical stimulation can be applied to the human P at an appropriate timing from the viewpoint of maintaining an appropriate posture by considering the movement state thereof. Specifically, when the leg is about to step on the ground or is stepping on the ground, it is possible to provide a sufficient strength in the leg to step on the ground in order to support the body weight of the human P by applying the electrical stimulation to the leg (refer to FIGS. 6(a) to 6(e)). Thereby, the human P may continue the periodical walking movement while maintaining the posture thereof under the assistance of the movement assist device 10. Thus, it is possible to assist stably the periodical movement of the human P even though the partial body is paralyzed or the body function is degraded due to neuropathy or the like.

Figure 7:
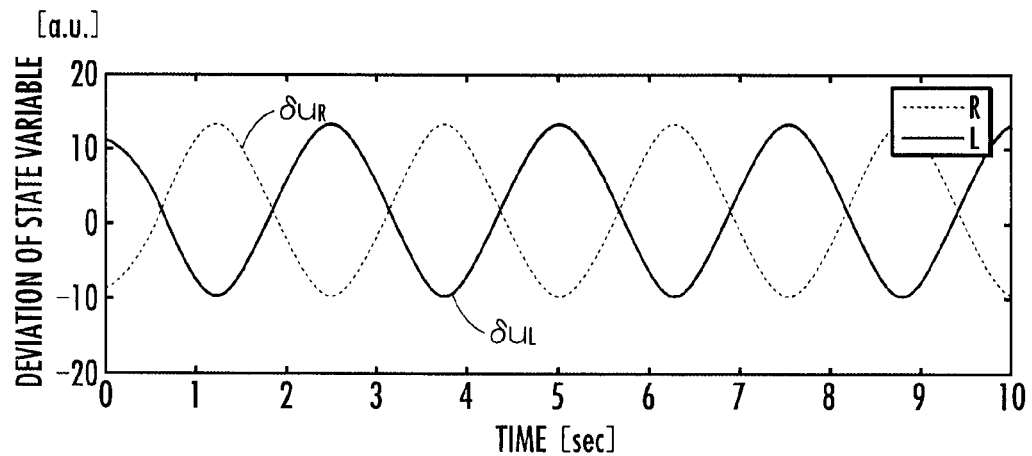
FIG. 7(*a*) is an explanatory diagram of a determination result on a deviation of state variables.
Figure 7:
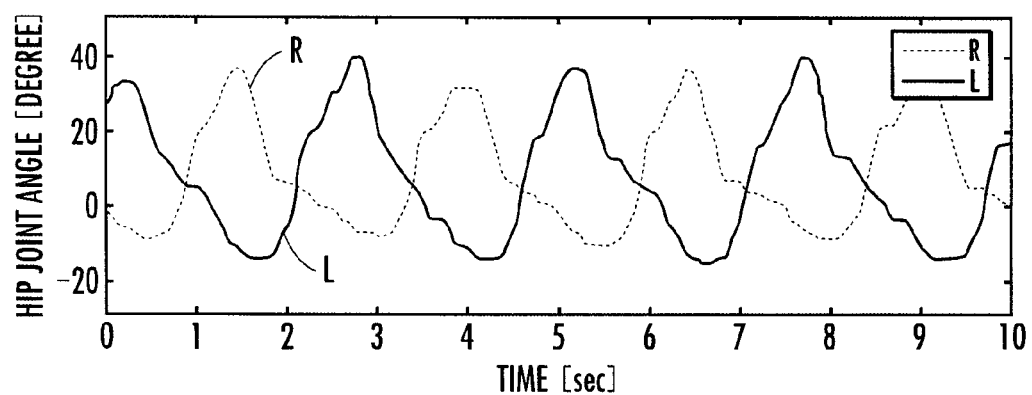
Figure 7:
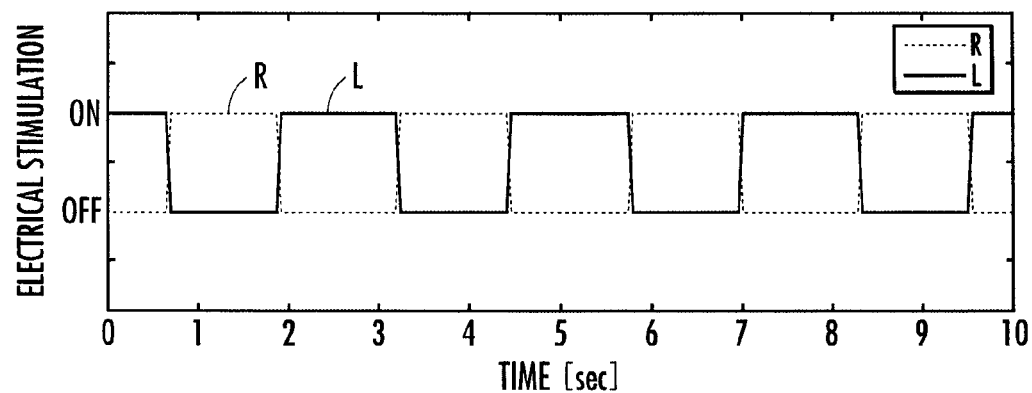

The determination results for the deviation $du_L$ and $du_R$ of the value of the state variable $u_i$ defining the second model, the left hip joint angle and the right hip joint angle, and the ON/OFF of the electrical stimulation applied to the human P by the electrical stimulation device 20, respectively, are shown respectively in FIG. 7(a) to FIG. 7(c) when the human P is in the walking movement state while assisted by the movement assist device 10. It is clear by viewing the figures that the deviation varying periodically illustrated in FIG. 7(a) and the hip joint angle varying periodically illustrated in FIG. 7(b) have such a correlation that the period therebetween is substantially identical and the phase difference therebetween is substantially constant. It is clear that there is also such a correlation that the period between the deviation or the hip joint angle, and the ON/OFF of the electrical stimulation varying periodically, as illustrated in FIG. 7(c), which is adjusted according to the deviation is substantially identical and the phase difference therebetween is substantially constant.

Figure 8:
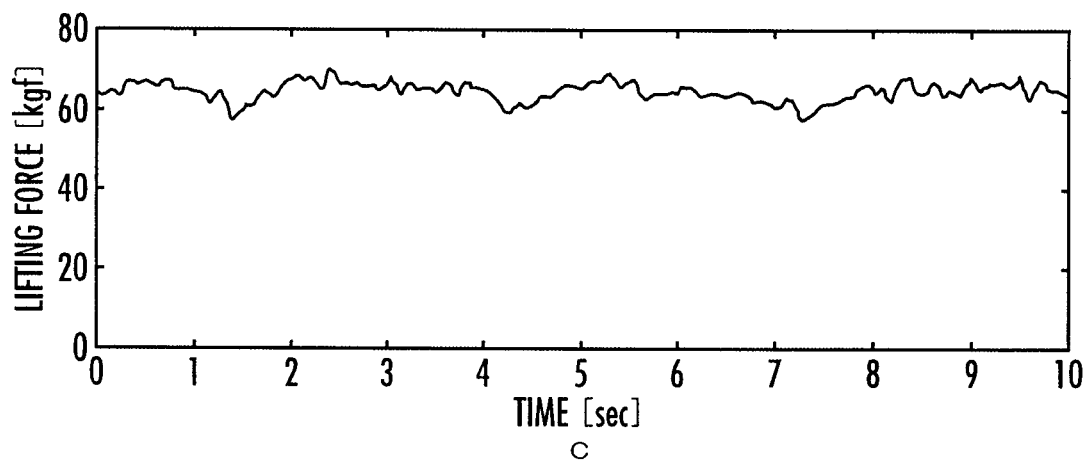
FIG. 8(*a*) is an explanatory diagram of a determination result on a lifting force without an electrical stimulation being applied.
Figure 8:
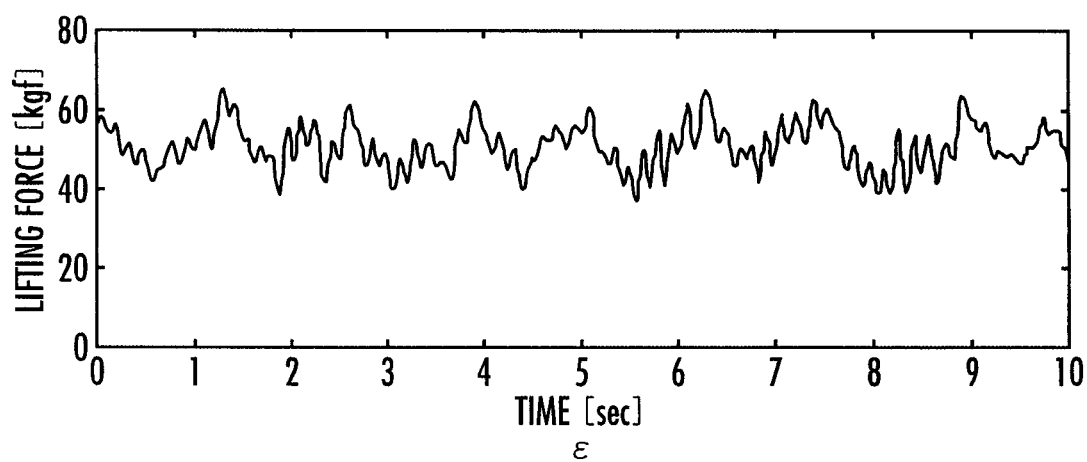
Figure 12:
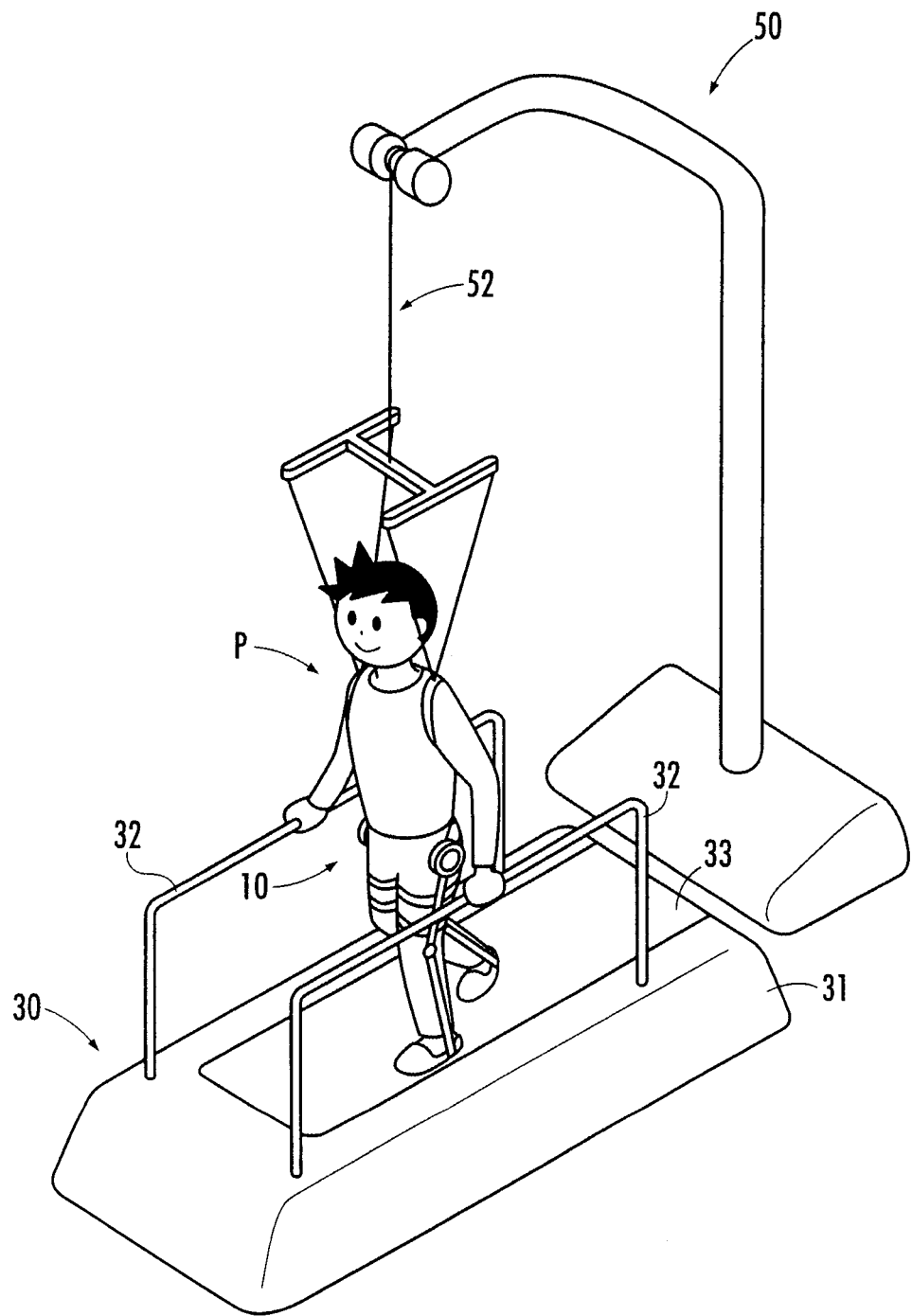
FIG. 12 is an explanatory diagram concerning one walking training method.

The determination results on lifting force of the human P in one case where an electrical stimulation is definitely not applied to the human P, and in the other case where an electrical is applied to the human P by controlling the ON/OFF of the electrical stimulation as illustrated in FIG. 7(c), are illustrated in FIG. 8(a) and FIG. 8(b), respectively. For example, the tension of a wire 52 of a lifter 50 illustrated in FIG. 12 is determined as the lifting force of the human P. In this instance, a rolling length of the wire 52 is adjusted by the lifter 50 so that the two feet of the human P may reach the ground. In cases where the electrical stimulation is not applied to the human P, the lifting force of the human P varied insignificantly around 60 kgf over time, as illustrated in FIG. 8(a). On the other hand, in cases where the electrical stimulation is applied to the human P, the lifting force of the human P varied periodically in a range of about 40 to 60 kgf over time, as illustrated in FIG. 8(b). That is to say that the lifting force of the human P is smaller in the case where the electrical stimulation is applied to the human P than in the case where the electrical stimulation is not applied to the human P. The fact that the lifting force becomes smaller means that the feet of the human P receives a reaction force from the ground. According to the experimental result, it is clear that a physical strength can be produced by applying an electrical stimulation according to the movement assisting system of the present embodiment in the foot for stepping on ground at an appropriate timing. Additionally, in the case where the stepping strength is weak, it is acceptable to use a load alleviation device in the walking training which will be described hereinafter so as to stabilize the posture of the human P (refer to FIGS. 12 and 13).

A movement assist system as a second embodiment of the present invention includes a movement assist device 10 and an electrical stimulation device 20.

Figure 9:
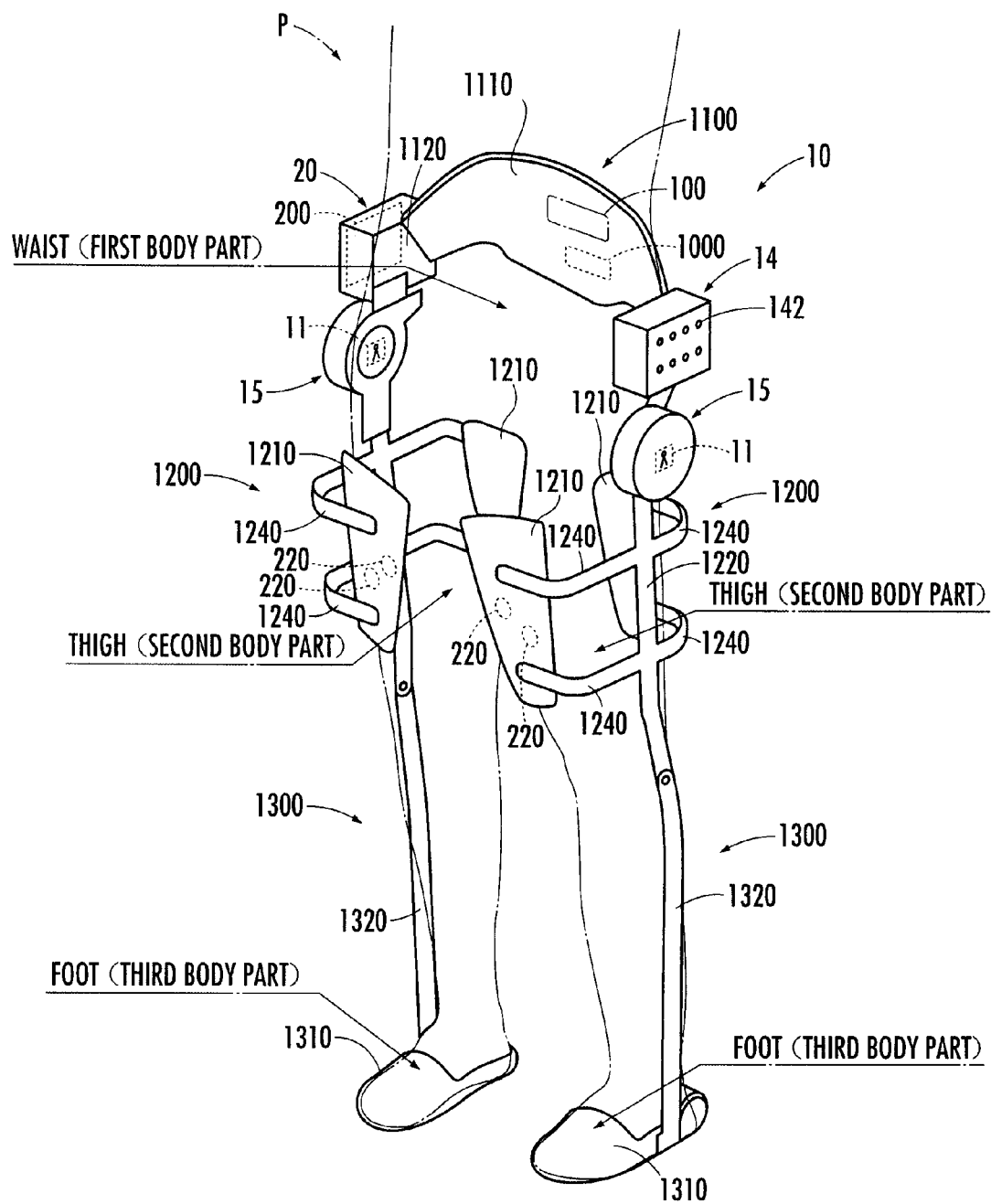
FIG. 9 is an explanatory diagram illustrating a configuration of a movement assist system as a second embodiment of the present invention.
Figure 10:
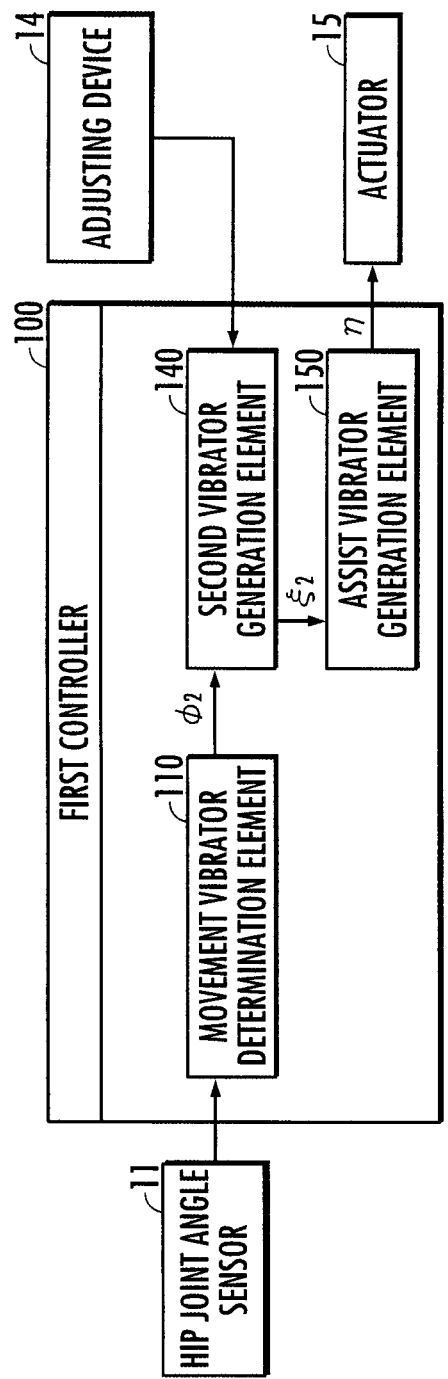
FIG. 10 is an explanatory diagram illustrating a configuration of a controller of the movement assist device in the second embodiment.

The movement assist device 10 illustrated in FIG. 9 has substantially identical configuration with the movement assist device 10 in the first embodiment of the present invention illustrated in FIG. 10. Therefore, the same numerals are used to refer to identical parts and descriptions thereof are omitted. The movement assist device 10 in the second embodiment of the present invention includes an adjusting device 14 having a plurality of adjusting buttons 14 for adjusting values of a time constant to be described hereinafter or the like. Note that it is acceptable to appropriately dispose the adjusting device 14 in the movement assist device 10 so that it is convenient to be operated by the human P or a supervisor who supervises the walking training of the human P.

A first controller 100 in the second embodiment of the present invention, as illustrated in FIG. 10, includes a movement vibrator determination element 110, a second vibrator generation element 140, and an assist vibrator generation element 150. In other words, the first controller 100 in the second embodiment of the present invention is constituted by omitting the movement variable determination element 102, the first movement vibrator generation element 120 and the intrinsic angular velocity setting element 130 from the first controller 100 in the first embodiment of the present invention as illustrated in FIG. 2. Each element may consist of a mutually different CPU or the like, or a universal CPU or the like.

The movement vibrator determination element 110 determines each hip joint angle as the second movement vibrator $\phi_2$ on the basis of an output from the hip joint angle sensor 11. In the second embodiment, the first movement vibrator $\phi_1$ is not determined. The second vibrator generation element 140 generates the second vibrator $\xi_2$ as the output vibration signal by inputting to the second model the second movement vibrator $\phi_2$ determined by the movement vibrator determination element 110 as the input vibration signal. The second model in the second embodiment is defined by the simultaneous equations (30) and is therefore identical to the second model in the first embodiment on this point. However, the second model in the second embodiment is different from the second model in the first embodiment in that the time constant $t_1 = \{t_{1i} | i = L+, L-, R+, R-\}$ and the coefficient $c = \{c_i | i = L+, L-, R+, R-\}$ of the desired value $\zeta_0 = \{\zeta_{0i} | i = L+, L-, R+, R-\}$ of the movement variable $\zeta$ representing the movement scale of the human P are adjusted via the operations on the adjusting button 142 in the second model in the second embodiment while the coefficient c is adjusted on the basis of the deviation between the determination value of the movement variable $\zeta$ and the desired value $\zeta_0$ in the second model in the first embodiment (refer to the equation (28) and FIG. 3/S038). Further, the second model in the second embodiment differs from the second model in the first embodiment in that the second intrinsic angular velocity $\omega_2$ contained in the second model in the second embodiment is adjusted indirectly by adjusting the time constant $t_{1i}$ (refer to the equation (31)) while the second intrinsic angular velocity $\omega_2$ is set according to the virtual model in the second model in the first embodiment. Similar to that in the first embodiment, the assist vibrator generation element 150 generates the assist vibrator η for defining the variation pattern of the torque applied to the thigh from the actuator 15 of the movement assist device 10 on the basis of the second vibrator $\xi_2$ generated by the second vibrator generation element 140.

The electrical stimulation device 20 in the second embodiment as illustrated in FIG. 9 has an identical configuration to that of the electrical stimulation device 20 in the first embodiment as illustrated in FIG. 1.

Hereinafter, descriptions will be given on functions of a movement assist system including the movement assist device 10 and the electrical stimulation device 20 having the aforementioned configurations in the second embodiment of the present invention. Firstly, descriptions will be given on the control method on the operation of the movement assist device 10 by the first controller 100.

Figure 11:
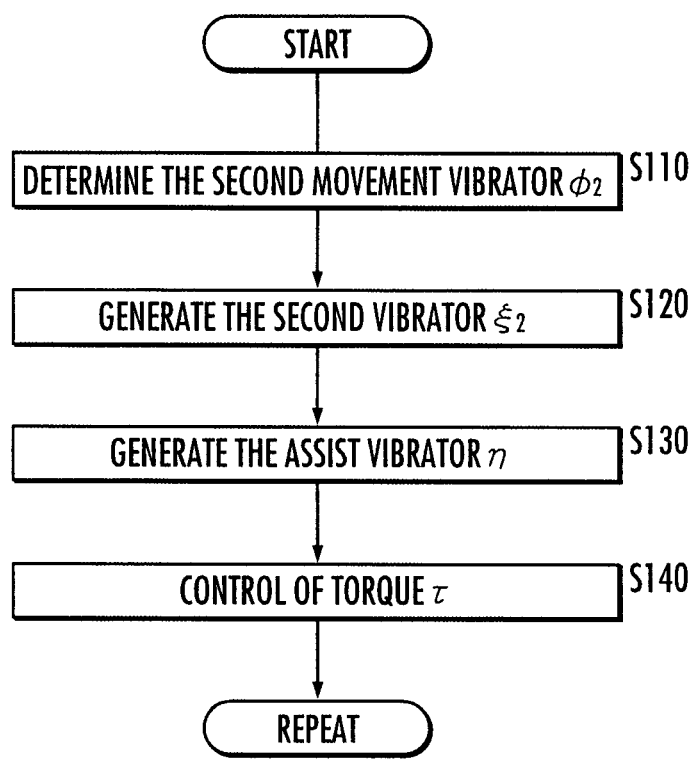
FIG. 11 is an explanatory diagram concerning a movement assist method in the second embodiment.

The movement vibrator determination element 110 determines the left hip joint angle and the right hip joint angle of the human P as the second movement vibrator $\phi_2 = (\phi_{2L}, \phi_{2R})$ on the basis of the output from the hip joint angle sensor 11 (FIG. 11/S110). Next, the second vibrator generation element 140 generates the second vibrator $\xi_2 = \{\xi_{2i} | i = L+, L-, R+, R-\}$ as the output vibration signal by inputting to the second model the movement vibrator $\phi_2$ determined by the movement vibrator determination element 110 as the input vibration signal (FIG. 11/S120). As mentioned above, the values of the time constant $t_{1i}$ and the coefficient $c_i$ relative to the desired value $\zeta_0$ of the movement variable $\zeta_i$ in the simultaneous equations

(30) may be varied by the operations on the adjusting button 142 of the adjusting device 14. Note that it is acceptable to change the values of the time constant $t_2=\{t_{2i}|i=L+, L-, R+, R-\}$, the correlation coefficient $w_{i/j}$ or the like in addition to or alternative to the time constant $t_{1i}$ or the coefficient $c_i$ via the adjusting device 14.

Thereafter, similar to the first embodiment, the assist vibrator $\eta=(\eta_L, \eta_R)$ is set by the second vibrator generation element 140 on the basis of the second vibrator $\xi_2$ (FIG. 11/S130). Subsequently, the torque $T=(T_L, T_R)$ applied to the human P from the movement assist device 10 is adjusted through the first orthosis 1100 and the second orthosis 1200 (FIG. 11/S140). Thereafter, the series of the aforementioned processes are performed repeatedly. Note that it is acceptable to control the motion of the movement assist device 10 irrelative to the aforementioned control method on the condition that the thigh is appropriately moved with respect to the waist in a duration from the initiation of the walking movement of the human P to the finish of 2-3 steps of the walking movement.

The control method of the electrical device 20 by the second controller 200 in the second embodiment is identical to that in the first embodiment (refer to FIG. 4), and therefore the descriptions thereof are omitted.

According to the movement assist system in the second embodiment of the present invention which performs the aforementioned functions, the second orthosis 1200 is moved by the actuator 15 with respect to the first orthosis 1100 as illustrated in FIGS. 5(a) and 5(b), and the third orthosis 1300 is moved by following the movement of the second orthosis 1200. Consequently, in addition to the period movement of the thigh (the second body part) being assisted with respect to the waist (the first body part), the lower leg (the third body part) is assisted so as to follow the thigh in moving. As a result, the periodical walking movement of the human P is assisted so that the scale and rhythm of the walking movement matches the desired scale and the desired rhythm of the movement, respectively.

Since no other model but the second model is used, therefore the arithmetic processing load needed to generate the second vibrator may be alleviated accordingly. Further, the time constant $t_1=\{t_{1i}|i=L+, L-, R+, R-\}$ and the coefficient $c=\{c_i|i=L+, L-, R+, R-\}$ contained in the simultaneous equations (refer to the equation (30)) for defining the second are partially adjusted via the operations on the button 142 of the adjusting device 14. Thereafter, the second vibrator $\xi_2$ is generated according to the adjusted second model and the output torque T which varies periodically and is applied to the human P is controlled on the basis of the second vibrator $\xi_2$ (refer to S130 and S140 in FIG. 11). Accordingly, the periodical movement of the human P can be assisted by applying a force to the human P so as to make the movement scale and movement rhythm thereof match the desired movement scale and the desired movement rhythm, respectively, with an attempt to alleviate the arithmetic processing load. Furthermore, the variation pattern of the second vibrator $\xi_2$ (angular velocity) and the variation pattern of the output torque T from the actuator 15 are adjusted by adjusting the time constant $t_{1i}$ representing the variation pattern of the state variable $u_i$. Thereby, the periodical movement of the human P may be assisted so as to make the movement rhythm of the human P assisted by the torque T approximate to the desired movement rhythm. Additionally, the magnitude of the second vibrator $\xi_2$ and the magnitude of the output torque T from the actuator 15 may be adjusted by adjusting the coefficient $c_i$ relative to the desired value $\zeta_0$ of the movement variable $\zeta$. Thereby, the periodical movement of the human P may be assisted so as to approximate the movement scale thereof to the desired movement scale.

Similar to the first embodiment, it is possible for the electrical stimulation device 20 in the second embodiment to assist stably the periodical movement of the human P whose partial body is paralyzed or whose body function is degraded due to neuropathy or the like (refer to FIGS. 6(a) to 6(e) and FIG. 8(b)).

In addition, it is described in the aforementioned embodiments that the movement of the human P is assisted. However, it is also possible to assist the walking movement of an animal such as a monkey (and/or ape), a dog, a horse, cattle or the like other than a human.

In the aforementioned embodiment, the movement assist device 10 is constituted to assist the walking movement of the human P (refer to FIG. 1), it is acceptable to constitute the movement assist device 10 by varying the material, shape or the like of the first orthosis 1100, the second orthosis 1200 and the third orthosis 1300 so as to be attached to various body parts of the human P to assist various periodical movement except the walking movement as an embodiment. For example, it is acceptable to assist a periodical movement of the forearm with respect to the brachium. Moreover, it is acceptable to assist a periodical movement of the brachium with respect to the thigh of the human P.

In the aforementioned embodiment, the timing of the electrical stimulation applied to the human P from the electrical stimulation device 20 on the basis of the output signal representing the arithmetic processing result of the second vibrator generation element 140 of the first controller 100 is controlled by the second controller 200. It is also acceptable to control by the second controller 200 the timing of the electrical stimulation applied to the human P from the electrical stimulation device 20 on the basis of the first vibrator generation element 120 of the first controller 100 or the output signal representing the arithmetic processing result of the angular velocity setting element 130. Moreover, it is acceptable to control the timing of the electrical stimulation applied to the human P from the electrical stimulation device 20 by the second controller 200 on the basis of an output signal of the hip joint angle sensor 11, or a variation pattern of an output signal representing an acceleration in the vertical direction of the human P from an acceleration sensor attached thereto. Since a transition pattern between the stepping-on-ground state and the leaving-ground state of each foot of the human P may be estimated on the basis of the variation pattern of the output signal from the sensor, it is possible to apply an electrical stimulation to the human P at an appropriate timing and magnitude from the viewpoint of maintaining an appropriate posture by considering the periodical movement state of the human P whose body function is degraded.

The present invention is not limited to the movement assist device 10 to be used in the walking training of the human P as illustrated in FIG. 12, it is also possible to be used as a treadmill 30 and a lifter (a load alleviation tool) 50. The human P performs the walking movement so as to advance forward against the movement of an endless belt 33 which is moving backward with the partial weight thereof supported by a handrail (load alleviation tool) 32 which is disposed at both sides of a base 31 of the treadmill 30 by holding with both hands thereon. The endless belt 33 is supported over a plurality of rollers and the speed of the endless belt 33 is controlled by controlling the rotation velocity of a part of the plurality of rollers. Additionally, the partial weight of the human P is supported by a wire 52 whose winding amount is adjusted by the lifter 50.

Figure 13:
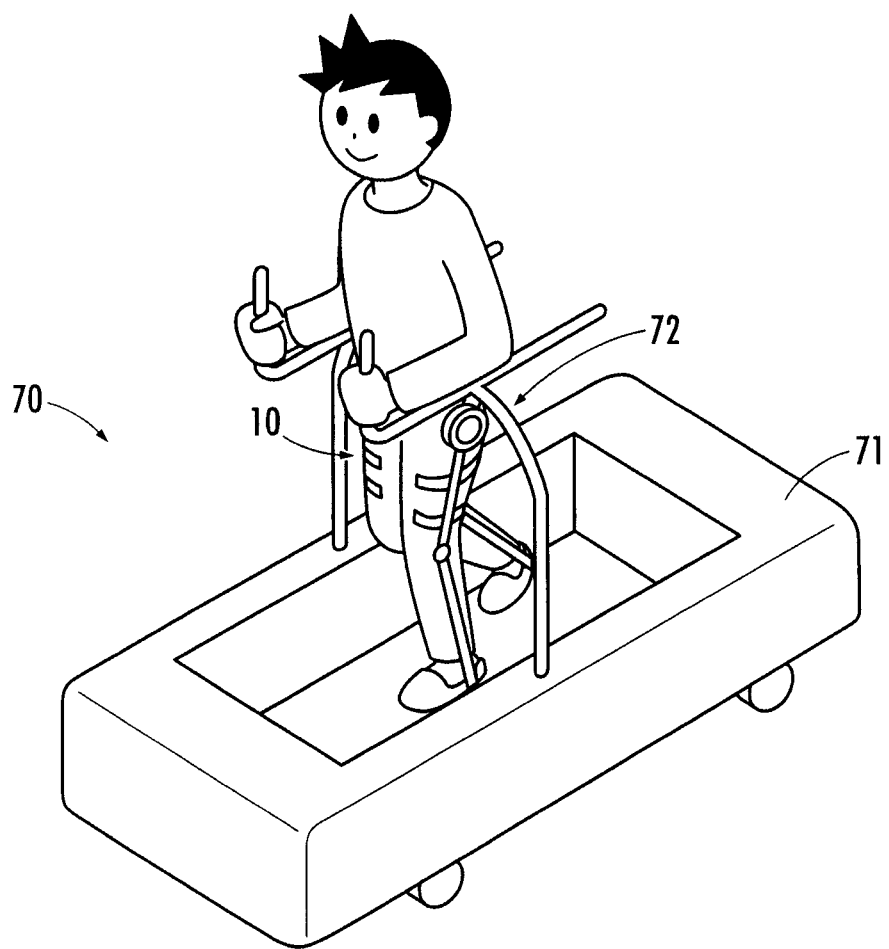
FIG. 13 is an explanatory diagram concerning another walking training method.

Furthermore, a walking machine 70 as illustrated in FIG. 13 may be used in the walking training of the human P. The partial weight of the human P is supported by a handrail (load alleviation tool) 72 which is disposed at both sides of a base 71 of the walking machine 70 by holding with both hands thereon. The base 71 can move in accordance with the walking movement of the human P, while controlling the rotation speed of wheels disposed at the bottom thereof.

Although the present invention has been explained in relation to the preferred embodiments and drawings but not limited, it should be noted that other possible modifications and variations made without departing from the gist and scope of the invention will be comprised in the present invention. Therefore, the appended claims encompass all such changes and modifications as falling within the gist and scope of the present invention.

What is claimed is:

1. A movement assist system for assisting a creature in moving, comprising:
    an ambulatory movement assist device configured to assist the creature during walking; and
    an electrical stimulation device;
    wherein the ambulatory movement assist device includes an orthosis mounted on the creature, an actuator connected to the orthosis, a movement sensor configured to sense a state of movement of the creature, and a first controller configured to control an amplitude and a phase of an output from the actuator, and to assist the creature in a periodical walking movement by applying an output which varies periodically from the actuator to the creature via the orthosis;
    the electrical stimulation device includes an electrode attached to the creature and a second controller configured to adjust an electrical stimulation applied to the creature on the basis of at least one of an output signal from the first controller and an output signal representing a movement state of the creature from the movement sensor, and wherein the electrical stimulation device assists the creature in producing a physical strength by applying the electrical stimulation to the creature via the electrode;
    the first controller includes: a movement vibrator determination element configured to determine a second movement vibrator which varies periodically according to a physical movement of the creature; and a second vibrator generation element configured to generate a second vibrator as an output vibration signal from a second model by inputting the second movement vibrator determined by the movement vibrator determination element as an input vibration signal to the second model which generates the output vibration signal varying at a specific angular velocity defined according to a second intrinsic angular velocity on the basis of the input vibration signal, the second vibrator serving as a control basis on the output of the actuator; and
    the second controller is configured to adjust the electrical stimulation applied to the creature on the basis of the output signal from the first controller which represents an arithmetic processing result of the second vibrator generation element.

2. The movement assist system according to claim 1, wherein
    the movement vibrator determination element is configured to determine a first movement vibrator which varies periodically according to the physical movement of the creature;
    the first controller includes
    a first vibrator generation element configured to generate a first vibrator as an output vibration signal from a first model by inputting the first movement vibrator determined by the movement vibrator determination element as an input vibration signal to the first model which generates the output vibration signal varying at a specific angular velocity defined according to a first intrinsic angular velocity on the basis of the input vibration signal by entraining to the input vibration signal; and
    an intrinsic angular velocity setting element configured to set an angular velocity of a second virtual vibrator as the second intrinsic velocity according to a virtual model representing a first virtual vibrator and the second virtual vibrator which interact and vary periodically with a second phase difference on the basis of a first phase difference between the first movement vibrator determined by the movement vibrator determination element and the first vibrator generated by the first vibrator generation element so as to approximate the second phase difference to a desired phase difference.

3. The movement assist system according to claim 1, wherein
    the first controller includes a movement variable determination element configured to obtain a determination value of a movement variable which represents a scale magnitude of the periodical movement of the creature; and
    the second vibrator generation element is configured to correct the second model so as to approximate the determination value of the movement variable determined by the movement variable determination element to a desired value.

4. The movement assist system according to claim 3, wherein
    the second model is defined by a simultaneous differential equation having multiple state variables representing a behavior state of the creature, which contains a product of the desired value of the movement variable and a coefficient; and
    the second vibrator generation element is configured to generate the second vibrator on the basis of values of the state variables obtained by solving the simultaneous differential equation, and to correct the second model by correcting the coefficient so as to approximate the determination value of the movement variable obtained by the movement variable determination element to the desired value.

5. The movement assist system according to claim 1, further including an adjusting device, wherein the second model is defined by a simultaneous differential equation which includes multiple state variables representing a behavior state of the creature, and the value of a member or a coefficient in the simultaneous differential equation is adjusted by the adjusting device.

6. The movement assist system according to claim 5, wherein the simultaneous differential equation for defining the second model includes a time constant representing a variation pattern of the state variables; and the value of the time constant is adjusted by the adjusting device.

7. The movement assist system according to claim 5, wherein the simultaneous differential equation for defining the second model includes a coefficient relative to the desired value of the movement variable representing the movement scale of the creature; and the value of the coefficient is adjusted by the adjusting device.

* * * * *